(12) United States Patent
Annis et al.

(10) Patent No.: US 8,703,164 B2
(45) Date of Patent: Apr. 22, 2014

(54) COMPOSITIONS FOR INACTIVATING PATHOGENIC MICROORGANISMS, METHODS OF MAKING THE COMPOSITIONS, AND METHODS OF USE THEREOF

(75) Inventors: Ted C. Annis, Ann Arbor, MI (US); James R. Baker, Ann Arbor, MI (US); Tarek Hamouda, Milan, MI (US)

(73) Assignee: NanoBio Corporation, Ann Arbor, MI (US)

( * ) Notice: Subject to any disclaimer, the term of this patent is extended or adjusted under 35 U.S.C. 154(b) by 1397 days.

(21) Appl. No.: 11/930,535

(22) Filed: Oct. 31, 2007

(65) Prior Publication Data

US 2012/0171249 A1 Jul. 5, 2012

Related U.S. Application Data

(63) Continuation of application No. 11/080,629, filed on Mar. 16, 2005, which is a continuation of application No. 11/067,626, filed on Feb. 28, 2005, now abandoned, which is a continuation of application No. 10/860,582, filed on Jun. 4, 2004, now abandoned.

(60) Provisional application No. 60/475,633, filed on Jun. 4, 2003.

(51) Int. Cl.
*A01N 25/00* (2006.01)
*A01N 33/12* (2006.01)
*A61K 9/00* (2006.01)

(52) U.S. Cl.
USPC ........... 424/405; 424/400; 424/757; 424/450; 424/489; 514/938; 514/937; 514/642

(58) Field of Classification Search
USPC .......... 514/937, 938, 642, 643; 424/400, 405, 424/489, 450, 757, 750, 727, 768
See application file for complete search history.

(56) References Cited

U.S. PATENT DOCUMENTS

| | | |
|---|---|---|
| 3,912,666 A | 10/1975 | Spitzer et al. |
| 3,954,967 A | 5/1976 | Urton |
| 4,020,183 A | 4/1977 | Asculai et al. |
| 4,262,007 A | 4/1981 | Sherrill |
| 4,451,267 A | 5/1984 | Schwab et al. |
| 4,481,188 A | 11/1984 | Apontoweil et al. |
| 4,540,573 A | 9/1985 | Neurath et al. |
| 4,599,088 A | 7/1986 | Davis et al. |
| 4,895,452 A | 1/1990 | Yiournas et al. |
| 4,909,940 A | 3/1990 | Horowitz et al. |
| 5,073,372 A | 12/1991 | Turner et al. |
| 5,103,497 A | 4/1992 | Hicks |
| 5,108,660 A | 4/1992 | Michael |
| 5,118,528 A * | 6/1992 | Fessi et al. ............... 427/213.36 |
| 5,152,923 A * | 10/1992 | Weder et al. ..................... 516/56 |
| 5,186,945 A | 2/1993 | Shanbrom |
| 5,188,822 A | 2/1993 | Viccaro et al. |
| 5,368,837 A | 11/1994 | Baker et al. |
| 5,380,530 A | 1/1995 | Hill |
| 5,405,602 A | 4/1995 | Simmons et al. |
| 5,405,604 A | 4/1995 | Hall |
| 5,510,104 A | 4/1996 | Allen |
| 5,547,677 A | 8/1996 | Wright |
| 5,549,901 A | 8/1996 | Wright |
| 5,618,840 A | 4/1997 | Wright |
| 5,635,491 A | 6/1997 | Seki et al. |
| 5,651,959 A | 7/1997 | Hill et al. |
| 5,656,280 A | 8/1997 | Herb et al. |
| 5,662,932 A | 9/1997 | Amselem et al. |
| 5,662,957 A | 9/1997 | Wright |
| 5,700,679 A | 12/1997 | Wright |
| 5,709,879 A | 1/1998 | Barchfeld et al. |
| 5,902,227 A | 5/1999 | Rivas |
| 5,925,341 A * | 7/1999 | Cervantes et al. .......... 424/78.03 |
| 5,942,237 A | 8/1999 | Gizurarson et al. |
| 5,951,988 A | 9/1999 | Littel-van den Hurk et al. |
| 5,961,958 A | 10/1999 | Homola et al. |
| 5,961,970 A | 10/1999 | Lowell et al. |
| 5,985,309 A | 11/1999 | Edwards et al. |
| 5,997,904 A | 12/1999 | Magdassi et al. |
| 6,015,832 A | 1/2000 | Baker, Jr. et al. |
| 6,039,936 A | 3/2000 | Restle et al. |
| 6,113,921 A | 9/2000 | Friedman et al. |
| 6,117,415 A | 9/2000 | Schwarz |
| 6,127,364 A | 10/2000 | Dyker et al. |
| 6,147,047 A | 11/2000 | Robbins et al. |

(Continued)

FOREIGN PATENT DOCUMENTS

DE 199 18 324 A1 10/2000
EP 0 278 996 A1 8/1988

(Continued)

OTHER PUBLICATIONS

Office Action in related U.S. Appl. No. 11/067,626, dated Oct. 13, 2009.
Office Action in related U.S. Appl. No. 11/080,629, dated Dec. 15, 2009.
Alasri et al., "Sporicidal properties of peracetic acid and hydrogen peroxide, alone and in combination, in comparison with chlorine and formaldehyde for ultrafiltration membrane disinfection." Can. J. Microbiol 1993; 39: 52-60.
Baragi et al., "Transplantation of transdiced Chondrocytes protects articular cartilage from intedeukin 1-induced extracellular matrix degradation." J Clin Invest 1995;96: 2454-2460.

(Continued)

*Primary Examiner* — Sreeni Padmanabhan
*Assistant Examiner* — Irina Neagu
(74) *Attorney, Agent, or Firm* — Foley & Lardner LLP

(57) ABSTRACT

Nanoemulsion compositions with low toxicity that demonstrate broad spectrum inactivation of microorganisms or prevention of diseases are described. The nanoemulsions contain an aqueous phase, an oil phase comprising an oil and an organic solvent, and one or more surfactants. Methods of making nanoemulsions and inactivating pathogenic microorganisms are also provided.

5 Claims, 5 Drawing Sheets

(56) References Cited

U.S. PATENT DOCUMENTS

| | | | |
|---|---|---|---|
| 6,165,500 | A | 12/2000 | Cevc |
| 6,299,884 | B1 | 10/2001 | Van Nest et al. |
| 6,337,324 | B1 | 1/2002 | Harmenberg et al. |
| 6,348,187 | B1 | 2/2002 | Pan et al. |
| 6,348,503 | B1 | 2/2002 | Squires |
| 6,355,229 | B1 | 3/2002 | Adamy |
| 6,361,787 | B1 | 3/2002 | Shaheen et al. |
| 6,391,288 | B1 | 5/2002 | Miyazawa et al. |
| 6,440,429 | B1 | 8/2002 | Torizuka et al. |
| 6,506,803 | B1 | 1/2003 | Baker, Jr. et al. |
| 6,541,001 | B1 | 4/2003 | Gallili et al. |
| 6,559,189 | B2 | 5/2003 | Baker, Jr. et al. |
| 6,635,676 | B2 | 10/2003 | Baker, Jr. et al. |
| 6,667,276 | B1 | 12/2003 | Maier et al. |
| 6,720,001 | B2 | 4/2004 | Chen et al. |
| 6,761,914 | B2 | 7/2004 | Deckers et al. |
| 6,793,929 | B2 | 9/2004 | Bleckmann et al. |
| 6,797,685 | B2 | 9/2004 | Zhu et al. |
| RE39,264 | E | 9/2006 | Harmenberg et al. |
| 2001/0028887 | A1 | 10/2001 | Douin et al. |
| 2002/0032134 | A1* | 3/2002 | Cauwet-Martin ............ 510/122 |
| 2002/0045667 | A1 | 4/2002 | Baker et al. |
| 2002/0119207 | A1 | 8/2002 | Baker et al. |
| 2002/0155084 | A1 | 10/2002 | Roessler et al. |
| 2003/0171344 | A1 | 9/2003 | Lekare |
| 2003/0175221 | A1 | 9/2003 | Gers-Barlag et al. |
| 2003/0194412 | A1 | 10/2003 | Baker et al. |
| 2004/0115159 | A1 | 6/2004 | Tadlock et al. |
| 2004/0258701 | A1 | 12/2004 | Dominowski et al. |
| 2005/0013868 | A1 | 1/2005 | Brynjelsen et al. |
| 2005/0196416 | A1 | 9/2005 | Kipp et al. |
| 2006/0100288 | A1 | 5/2006 | Bague et al. |
| 2006/0110415 | A1 | 5/2006 | Gupta |
| 2006/0251684 | A1 | 11/2006 | Annis et al. |
| 2006/0257426 | A1 | 11/2006 | Baker et al. |
| 2007/0036831 | A1 | 2/2007 | Baker |
| 2007/0116709 | A1 | 5/2007 | O'Hagan et al. |

FOREIGN PATENT DOCUMENTS

| | | |
|---|---|---|
| EP | 0 832 649 A1 | 4/1998 |
| EP | 1 156 781 B1 | 11/2001 |
| EP | 1 655 021 A1 | 5/2006 |
| JP | 4-48925 A | 2/1992 |
| JP | 10265326 | 10/1998 |
| WO | WO 94/26252 A1 | 11/1994 |
| WO | WO 96/23409 A1 | 8/1996 |
| WO | WO 96/33725 A1 | 10/1996 |
| WO | WO 00/50006 | 8/2000 |
| WO | WO 00/64429 A1 | 11/2000 |
| WO | WO 01/49296 A1 | 7/2001 |
| WO | WO 01/91728 A2 | 12/2001 |
| WO | WO 02/051390 A2 | 7/2002 |
| WO | WO 02/080864 A1 | 10/2002 |
| WO | WO 03/000243 A1 | 1/2003 |
| WO | WO 2006/035416 A2 | 4/2006 |
| WO | WO 2006/110699 A1 | 10/2006 |
| WO | WO 2008/045107 A2 | 4/2008 |

OTHER PUBLICATIONS

Beauchamp et al., "A Critical review of the toxicology of glutaraldphyde." Crit. Rev. ToxicoL 1992; 22:143-174.
Berkelman et al., "Emerging infectious diseases in the United States, 1993." J Infect Dis. Aug. 1994; 170(2):272-7.
Burdon et al., "Experimental infection of mice with Bacillus cereus: studies of pathogenesis and pathologic changes." J. Infect. Dis. 1967; 117:307-316.
Burdon and Wende. "On the differentiation of anthrax bacilli from Bacillus cereus." J. Infect. Dis. 1960; 107: 224-234.
Dragon and Rennie "The ecology and anthrax spores: Tough but not invincible." Can. Vet. J. 1995; 36: 295-301.
Drobniewski "Bacillus cereus and related species." Clin. Microbiol. Rev. 1993; 6: 324-338.

Eriksson et al., "Virus validation of plasma-derived products produced by Pharmacia, with particular reference to immuno Globulins." Blood Coagulation and Fibtinolysis 1994; 5 (Suppl. 3): S37-S44.
Foster and Johnstone "Pulling the trigger: the mechanism of bacterial spore germination." MolecularMicrobiology 1990;4:137-141.
Franz et al., "Clinical recognition and management of patients exposed to biological warfare agents." JAMA 1997; 278: 399-411.
Fritz et al., "Pathology of experimental anthrax in'the rhesus monkey." Lab. Invest. 1995; 73: 691-702.
Graham et al., "Characteristics of a human cell line transformed by DNA from human adenovirus type 5." J Gen Virol 1977; 36: 59-74.
Halvorson and Church, Bacteriol Rev 1957, 21:112.
Hamouda et al., "Microbiocidal effects of liposome-like microemulsions on pathogenic Gram negative bacteria." In: American Society for Microbiology, 98th General Meeting, Atlanta, Georgia, U.S.A., 1998; Abstract A-52.
Hamouda et al., "A novel surfactant nanoemulsion with broad-spectrum sporicidal activity against Bacillus species". Journal Infectious Disease 1999. 180:1939-1949.
Hayden et al., "Plaque inhibition assay for drug susceptibility testing of influenza viruses." Antimicrob Agents Chemother. 1980 17: 865-870.
Herlocher et al., "Sequence comparison of AIAA/6/60 influenza viruses: mutations, which may contribute to attenuation." Virus Res. 1996; 42:11-25.
Hermonat et al., "The spermicide nonoxynol-9 does not inactivate papillomavirus." Sexually Trans Dis 1992; 19: 203-205.
Hess et al., "Epidermal toxicity of disinfectants." Amer. J. Dent. 1991; 4: 51-56.
Hills, J Gen Microbiol 4:38,1950.
Horowitz et al., "Solvent/detergent-treated plasma: a vi rus-in activated substitute for fresh frozen plasma." Blood 1992; 79: 826-831.
Huang et al., "Antiviral activity of some natural and synthetic sugar analogues." FEBS Letters. 1991; 291: 199-202.
Ivins et al., "Experimental anthrax vaccines: efficacy of adjuvants combined with protective antigen against an aerosol Bacillus anthracis spore challenge in guinea pigs." Vaccine 1995; 13: 1779-1784.
Jackson et al., "PCR analysis of tissue samples from the 1979 Sverdlovsk anthrax victims: The presence of multiple Bacillus anthracis strains in 10 different victims." PNAS 1998; 95:1224-1229.
Karalvanova and Spiro RG. "Sulphation of N-linked oligosacchaddes of vesicular stomatitis and influenza virus envelope glycoproteins: host cell specificity, subcellular localization and identification of substituted saccharides." Bioch J 1998; 329: 511-518.
Lamanna and Jones "Lethality for mice of vegetative and spore forms of Bacillus cereus and Bacillus cereus-like insect pathogens injected intraperitoneally and subcutaneously." J. Bact. 1963; 85: 532-535.
Lamb and Krug "Orthomyxoviride: The viruses and their replication." In: Fields BN. Knipe DM. Howley PM. eds. Fields Virology, 3rd ed., Philadelphia Pennsylvania, U.S.A., Lippincoft-Raven Publishers, 1996; 1353-1395.
Lee "Review: in vitro spermicidal tests." Contraception 1996; 54: 131-147.
Lim and Chae "A simple assay for DNA transfection by incubation of the cells in culture dishes with substrates for beta-galactosidase." Biotechniques 1989; 7: 576-579.
Lineaweaver et al., "Topical antimicrobial toxicity." Arch. Surg. 1985; 120: 267-270.
Mammen et al., "Effective inhibitors of hemagglutination by influenza virus synthesized from polymers having active ester groups. Insight into mechanism of inhibition." J Med Chem 1995; 38: 4179-4190.
Mendel et al., "Oral administration of a prodrug of the influenza virus neuraminidase inhibitor GS 4071 protects mice and ferrets against influenza infection." Antimicrob Agents Chemother 1998; 42: 640-646.
Meselson et al., "The Sverdlovsk anthrax outbreak of 1979." Science 1994; 266:1202-1208.

(56) References Cited

OTHER PUBLICATIONS

Mobley "Biological warfare in the twentieth century: lessons from the past, challenges for the future." Military Med. 1995; 160: 547-553.
Morgan "A brief review of formaldehyde carcinogenesis in relation to rat nasal pathology and human health risk assessment." ToxicoL PathoL 1997; 25: 291-307.
Mosmann J. Immun. Methods 1983, 65, 55-63 Mulder and Hers "Influenza." Wolter-Noordhoff Publishing, 1972.
O'Hagan "Recent advances in vaccine adjuvants for systemic and mucosal administration." J Pharmacy Pharmacol 1998; 50: 1-10.
Pile et al., "Anthrax as a potential biological weapon." Arch. Intern. Med. 1998; 158: 429-434.
Portocala et al., "Immunoelectrophoretic characterization of Sendai virus antigens." Virologie 1976; 27: 261-264.
Russell "Bacterial spores and chemical sporicidal agents." Clin. Micro 1990; 3: 99-119.
Schulze "Effects of glycolysation on the properties and functions of influenza virus hemagglutinin." J Infect Dis 1997; 176 (Suppl. 1): S24-28.
Shibata "Germination of inactivated spores of *Bacillus cereus* T. Effect of preincubation with L-alanine or inosine on the subsequent germination." Japan. J. Microbiol. 1976; 20: 529-535.
Smith et al., "Dihydropyrancarboxamides related to Zanamivir: a new series of inhibitors of influenza virus sialidases. 1. Discovery, synthesis biological activity, and structure-activity relationships of 4-guanidino and 4-amino-4H-pyran-6-carboxamides." J Med Chem 1998; 41: 787-797.
Titball and Manchee "Factors affecting the germination of spores of *Bacillus anthracis*." J. Appi. Bact. 1987; 62: 269-273.
Waghorn and Goa, "Zanamivir." Drugs 1998; 55: 721-725.
Welkos and Friedlander "Pathogenesis and genetic control of resistance to the Sterne strain of *Bacillus anthracis*." Microb. Path. 1988; 4: 53-69.
Yanagita, 1957, Arch Mikrobiol 26:329.
Zeitlin et al., "Tests of vaginal microbicides in the mouse genital herpes model." Contraception 1997; 56: 329-335.
Smyth et al., "The Place of the Range Finding Test in the Industrial Toxicology Laboratory," Journal of Industrial Hygiene and Toxicology, 26(8):269-273 (1944).
Windholtz et al., The Merck Index, published by Merck and Co. (Rahway, NJ), p. 1249, Abstract No. 8574 (1983).
Hamouda et al., Microbicidal Effects of Lipsome-Like Nanoemulsion on Pathogenic Gram Negative Bacteria, 98th ASM General Meeting, Atlanta, Abstract # A-52 p. 47 (11 pages).
Altemeier et al., "Chloromycetin and Aureomycin in Experimental Gas Gangrene," Surgery, Oct. 1950. vol. 28, No. 4, pp. 621-631.
Athanasiu et al., "Presence of specific antigen and alterations in enzyme activity in the chorio-allantoic membrane of embryonate hen eggs infected with influenze A2 or B virus," Rev. Ruon. Med.—Virol., vol. 27, No. 1, 1976, pp. 3-6.
Brown et al., "Differential diagnosis of *Bacillus Cereus, Bacillus Anthracis* and *Bacillus Cereus var. Mycoides*," Oct. 17, 1957, pp. 499-509.
Butterton et al., "Development of a Germfree Mouse Model of *Vibrio cholerae* Infection," Infection and Immunity, Oct. 1996, vol. 64, No. 10, pp. 4373-4377.
Carter et al., "The route of enteric infection in normal mice," J. Exp. Med., vol. 139, 1974, pp. 1189-1203.
Castleman et al., "Pathogenesis of brochiolitis and Pneumonia Induced in Neonatal and Weanling Rats by Parainfluenza (Sendai) Virus," American Journal of Pathology, vol. 129, No. 2, Nov. 1987, pp. 277-286.
Castleman et al., "Respiratory tract lesions in weanling outbred rats infected with Sendai virus," Am J. Vet. Res., vol. 44, No. 6, pp. 1024-1031.
Collins, F.M., "Salmonellosis in Orally Infected Specific Pathogen-Free C57B1 Mice," Infection and Immunity, Feb. 1972, vol. 5, No. 2, pp. 191-198.
Collins et al., "Comparative Immunogenicity of Heat-Killed and Living Oral *Salmonella* Vaccines," Infection and Immunity, Oct. 1972, vol. 6, No. 4, pp. 451-458.
Eriksson et al., "Virus validation of plasma-derived products produced by Pharmacia, with particular reference of immunoglobulins," Blood Coagulation and Fibrinolysis, vol. 5, Suppl. 3, 1994, pp. S37-S44.
Finkelstein et al., "Pathogenesis of experimental cholera in infant rabbits," 1964, J. Infect. Dis., vol. 114, pp. 203-216.
Formal et al., "Experimental *Shigella* Infections," J. Bacteriol., 1963, vol. 85, pp. 119-125.
Freter et al., "Experimental enteric *shigella* and vibrio infections in mice and guinea pigs," 1965, J. Exp. Med, vol. 104, No. 3, pp. 411-418.
Freter, Rolf, "The fatal enteric cholera infection in the guinea pig, achieved by inhibition of normal enteric flora," J. Infect. Dis., 1955, vol. 97, No. 1, pp. 57-65.
Hamouda et al., "Antimicrobial mechanism of action of surfactant lipid preparations in enteric Gram-negative bacilli," J. Appl. Microbiol., 2000, vo.. 89, pp. 397-403.
Jacoby et al., "Sendai viral pneumonia in aged BALB/c mice," Experimental Gerontology, vol. 29, No. 1, 1994, pp. 89-100.
Johnson et al., "Age-dependent Resistance to Viral Encephalitis: Studies of Infections due to Sindbis Virus in Mice," The Journal of Infectious Diseases, Mar. 1972, vol. 125, No. 3.
Johnson et al., "Virus invasion of the central nervous system," Jun. 1965, Am. J. Pathol., vol. 46, No. 6, pp. 929-943.
Labrec et al., "Epithelial cell penetration as an essential step in the pathogenesis of bacillary dysentery," Journal of Bacteriology, Nov. 1964, vol. 88, No. 5, pp. 1503-1518.
Levine et al., "New Knowledge on Pathogenesis of Bacterial Enteric Infections as Applied to Vaccine Development," Microbiological Reviews, Dec. 1983, vol. 47, No. 4, pp. 510-550.
Kamat, Nanoemulsions (p. 1-17), in 11/080,629.
Maha et al., "The effect of nonionic detergent on dengue and Japanese encephalitis virus antigens in antigen detection ELISAa and IgM-capture ELISA," Southeast Asian J. Trop. Med. Public Health, Dec. 1997, vol. 28, No. 4, pp. 718-722.
Massion et al., "Parainfluenza (Sendai) Virus Infects Ciliated Cells and Secretory Cells but Not Basal Cells of Rat Tracheal Epithelium," Am. J. Respir. Cell Mol. Biol., 1993, vol. 9, pp. 361-370.
McMichael, A., "Cytotoxic T Lymphocytes Specific for Influenza Virus," Cytotoxic T-Lymphocytes in Human Viral and Malaria Infections, 1994, pp. 75-91.
Mims et al., "Parainfluenza Virus Sendai Infection in Macrophages, Ependyma, Choroid Plexis, Vascular Endothelium and Respiratory Tract of Mice," American Journal of Pathology, Mar. 1973, vol. 70, No. 3, 315.
Mor et al., "Perspective: edible vaccines-a concept coming of age," Trends in Microbiology, Nov. 1998, vol. 6, No. 11, pp. 449-453.
Naughton et al., "A rat model of infection by *Salmonella typhimurium* or *Salm. Enteritidis*," Journal of Applied Bacteriology, 1996, vol. 81, pp. 651-656.
Perreault et al., Immunodominant minor histocompatibility antigens: the major ones, Immunology Today, Feb. 1998, vol. 19, No. 2, pp. 69-74.
Richter et al., "Transgenic Plants as Edible Vaccines," Cuff. Top. Microl. Immunol., 1999, vol. 240, pp. 159-176.
Ruedl et al., "Features of Oral Immunization," Int. Arch Allergy Immunol., 1995, vol. 108, pp. 334-339.
Sandusky et al., "An evaluation of aureomycin and chloromycetin in experimental *Clostridium welchii* infection," Surgery, Oct. 1950, vol. 28, No. 4, pp. 632-641.
Sercarz et al., "Dominance and crypticity of T cell antigenic determinants," Annu. Rev. Immunol., 1993, vol. 11, pp. 729-766.
Silins et al., "Development of Epstein-Barr Virus-specific Memory T Cell Receptor Clonotypes in Acute Infectious Mononucleosis," J. Exp. Med., Nov. 1996, vol. 184, pp. 1815-1824.
Steven et al., "Epitope Focusingin the Primary Cytotoxic T Cell Response to Epstein-Barr Virus and its Relationship to T Cell Memory," J. Exp. Med., Nov. 1996, vol. 184, pp. 1801-1813.
Stevens et al., Comparison of Single and Combination Antimicrobial Agents for Prevention of Experimental Gas Gangrene Caused by

(56) References Cited

OTHER PUBLICATIONS

*Clostridium perfringens*, Antimicrobial Agents and Chemotherapy, Feb. 1987, vol. 31, No. 2, pp. 312-316.

Stevens et al., "Comparison of Clindamycin, Rifampin, Tetracycline, Metronidazole, and Penicillin for Efficacy in Prevention of Experimental Gas Gangrene due to *Clostridium perfringens*," The Journal of Infectious Diseases, Feb. 1987, vol. 155, No. 2, pp. 220-228.

Takeuchi et al., "Experimental Bacillary Dysentery, an Electron Microscopic Study of the Response of the Intestinal Mucosa to Bacterial Invasion," Dec. 1965, vol. 47, No. 6, pp. 101044.11-.

Tremblay et al., "T lymphocyte responses to multiple minor histocompatibility antigens generate both self-major histocompatibility complex-restricted and cross-reactive cytotoxic T lymphocytes," Transplantation, Jul. 1994, vol. 58, No. 1, pp. 59-67.

Welkos et al., "Comparative safety and efficacy against *Bacillus anthracis* of protective antigen and live vaccines in mice," Microbial Pathogenesis, 1988, vol. 5, pp. 127-139.

Weiner, Drug Development and Industrial Pharmacy, 12 (7), 933-951 (1986), "Strategies for Formulation and Evaluation of Emulsions and Suspensions: Some Thermodynamic Considerations".

Weiner, Pharmaceutical Dosage forms: Disperse Systems, vol. 1, second edition, pp. 1-15, 1996.

Tarbox et al., "Benzalkonium Chloride," Clinical Orthopaedics and Related Research, No. 346, pp. 255-261, 1998.

Tevi-Benissan et al., "Protection of Cynomolgus Macaque Against Cervicovaginal Transmission of SIVmac251 by the Spermicide Benzalkonium Chloride," Journal of Acquired Immune Deficiency Syndromes, vol. 24, 2000, pp. 147-153.

Wadhams et al., "Efficacy of a Surfactant, Allantoin, and Benzalkonium Chloride Solution for Onychomycosis," Journal of the American Podiatric Medical Association, vol. 89, No. 3, Mar. 1999, pp. 126-130.

Wainberg et al., "Effect of benzalkonium chloride on HIV and related infections on other infectious agents," Arch. AIDS Res., vol. 1, No. 1, 1987, pp. 57-68 (Abstract —1 page).

Office Action in related U.S. Appl. No. 11/080,629, dated May 20, 2009.

Office Action cited in related U.S. Appl. No. 11/930,501, dated Aug. 25, 2011.

Office Action cited in related U.S. Appl. No. 11/930,523, dated Aug. 24, 2011.

Office Action cited in related U.S. Appl. No. 11/930,512, dated Aug. 23, 2011.

Office Action cited in related Chinese Patent Application No. 200980122725.5, dated Mar. 30, 2012.

Office Action cited in related U.S. Appl. No. 12/425,984, dated Nov. 28, 2011.

Theil et al., "Latent Herpes Virus Infection in Human Trigeminal Ganglia Causes Chronic Immune Response," American Journ. Of Pathology, vol. 163, No. 6, pp. 2179-2184 (2003).

Notice of Reasons for Rejected issued in related Japanese Patent Application No. 2011-505231, dated Sep. 17, 2013.

Hamouda et al., Development of a Novel Antifungal Drug (NB-001) for Topical Application in Humans (2008), 1 page.

\* cited by examiner

COMPOSITIONS FOR INACTIVATING PATHOGENIC MICROORGANISMS, METHODS OF MAKING THE COMPOSITIONS, AND METHODS OF USE THEREOF

CROSS-REFERENCE TO RELATED PATENT APPLICATIONS

This application is a continuation of co-pending U.S. patent application Ser. No. 11/080,629, which is a continuation of co-pending U.S. patent application Ser. No. 11/067,626, which is a continuation of U.S. patent application Ser. No. 10/860,582, which claims the benefit under 35 USC §119(e) of U.S. Application No. 60/475,633, filed Jun. 4, 2003, incorporated herein by reference in its entirety.

FIELD OF THE INVENTION

The present disclosure relates to compositions and methods for decreasing the infectivity, morbidity, and/or rate of mortality associated with a variety of pathogenic microorganisms.

BACKGROUND OF THE INVENTION

Pathogenic microorganisms such as bacteria, fungi, viruses, and bacterial spores are responsible for a plethora of human and animal ailments. In addition to vegetatively growing bacteria, bacteria of the *Bacillus* genus and others form stable spores that resist harsh conditions and extreme temperatures. For example, contamination of farmlands with *B. anthracis* can lead to a fatal disease in domestic, agricultural, and wild animals, as well as in humans in contact with infected animals or animal products. *B. anthracis* infection in humans is no longer common due to effective animal controls that include vaccines, antibiotics, and appropriate disposal of infected livestock. However, animal anthrax infection still represents a significant problem due to the difficulty of decontaminating land and farms. Moreover, *B. anthracis* spores can be used as a biological weapon. While an anthrax vaccine is available and can be used for the prevention of classic anthrax, genetic mixing of different bacterial strains can render it ineffective.

Other members of the *Bacillus* genus are also reported to be etiological agents for many human diseases. *B. cereus* is a common pathogen involved in food borne diseases due to the ability of the spores to survive cooking procedures. It is also associated with local sepsis, wound and systemic infection.

Although antibiotic and antimicrobial therapy is very effective and a mainstay of modern medicine, these therapies suffer from several disadvantages. For example, bacterial strains can develop antibiotic resistance. A person infected with an antibiotic resistant strain of bacteria faces serious and potentially life-threatening consequences because antibiotics cannot eliminate the infection. Pneumococci, which cause pneumonia and meningitis, *Salmonella* and *E. coli* which cause diarrhea, and enterococci which cause blood stream, surgical wound, and urinary tract infections can all develop antibiotic resistance resulting in fatal infections.

Moreover, antibiotics are not effective in eliminating or inactivating bacterial spores and viruses. Disinfectants and biocides, such as sodium hypochlorite, formaldehyde and phenols can be effective against bacterial spores, but are not well suited for decontamination of the environment, equipment, or casualties. The toxicity of these compounds can result in tissue necrosis and severe pulmonary injury following contact or inhalation of volatile fumes. Furthermore, the corrosive nature of commonly used disinfectants and biocides renders them unsuitable for decontamination of sensitive equipment.

Viruses are additional pathogens that infect human and animals which currently lack effective means of inactivation. For example, influenza A virus is a common respiratory pathogen widely used as a model system to test anti-viral agents in vitro and in vivo. The envelope glycoproteins of influenza A, hemagglutinin (HA) and neuraminidase (NA), which determine the antigenic specificity of viral subtypes, mutate readily, rendering antibodies incapable of neutralizing the virus. Current anti-viral compounds and neuraminidase inhibitors are minimally effective and viral resistance is common.

SUMMARY OF THE INVENTION

Accordingly, there remains a need in the art for anti-pathogenic compositions and methods that decrease the infectivity, morbidity, and/or mortality associated with pathogenic exposure while minimizing microbial resistance, toxicity to the recipient, and deleterious effects to equipment and the environment.

To address these and other needs, the present invention provides emulsions comprising an aqueous phase, an oil phase comprising an oil and an organic solvent, and at least one surfactant. The emulsion comprises particles preferably having an average diameter of less than 150 nm.

In one embodiment, the invention provides a method of reducing the average nanoemulsion particle size of a composition comprising a nanoemulsion, comprising treating a nanoemulsion comprising an aqueous phase, an oil phase comprising an oil and an organic solvent, and a surfactant, and having nanoemulsion particles of an average diameter of greater than or equal to about 250 nm, so as to reduce the average diameter of the nanoemulsion particles to less than 150 nm.

In another embodiment, the invention provides a method of making a nanoemulsion, comprising passing a first nanoemulsion through a high pressure homogenizer or a microfluidizer under conditions effective to reduce the average diameter of the nanoemulsion particles less than 150 nm. The nanoemulsion comprises an aqueous phase, an oil phase comprising an oil and an organic solvent, and one or more surfactants. The initial nanoemulsion particles have an average diameter of greater than or equal to about 250 nm.

The invention also provides a method of inactivating a microorganism, comprising contacting the microorganism with a composition comprising a nanoemulsion for a time effective to inactivate the microorganism. The nanoemulsion comprises an aqueous phase; an oil phase comprising an oil and an organic solvent and one or more surfactants. The nanoemulsion particles have an average diameter of less than 150 nm.

The invention further provides a method of inactivating a pathogenic microorganism comprising contacting a subject infected with the microorganism with a composition comprising a nanoemulsion. The nanoemulsion comprises an aqueous phase, an oil phase comprising an oil and an organic solvent, and one or more surfactants, wherein the nanoemulsion comprises particles having an average diameter of less than 150 nm.

In an additional embodiment, the invention provides an immunogenic composition comprising a nanoemulsion, wherein the nanoemulsion comprises an aqueous phase, an oil phase comprising an oil and an organic solvent, and a surfactant, wherein the nanoemulsion comprises nanoemulsion particles having an average diameter of less than or equal to about 250 nm and a microorganism or a portion thereof.

In a further embodiment, the invention provides method of vaccinating against a microorganism comprising administering to a subject the a composition comprising a nanoemulsion, wherein the nanoemulsion comprises an aqueous phase, an oil phase comprising an oil and an organic solvent, and one or more surfactants, wherein the nanoemulsion comprises particles having an average diameter of less than or equal to about 250 nm. The microorganism is inactivated by the composition and an immunological response by the subject is elicited.

In another embodiment, the invention provides a method of preventing an infected state caused by a microorganism, comprising administering to a subject, either before or after exposure to a microorganism, a composition comprising a nanoemulsion. The nanoemulsion comprises an aqueous phase, an oil phase comprising an oil and an organic solvent, and one or more surfactants, wherein the nanoemulsion comprises particles having an average diameter of less than 150 nm.

The invention further provides a kit comprising a composition comprising a nanoemulsion, wherein the composition is provided in a single formulation or a binary formulation, wherein the binary formulation is mixed prior to using the composition.

The above described and other features are exemplified by the following figures and detailed description.

DETAILED DESCRIPTION

Figure 1:
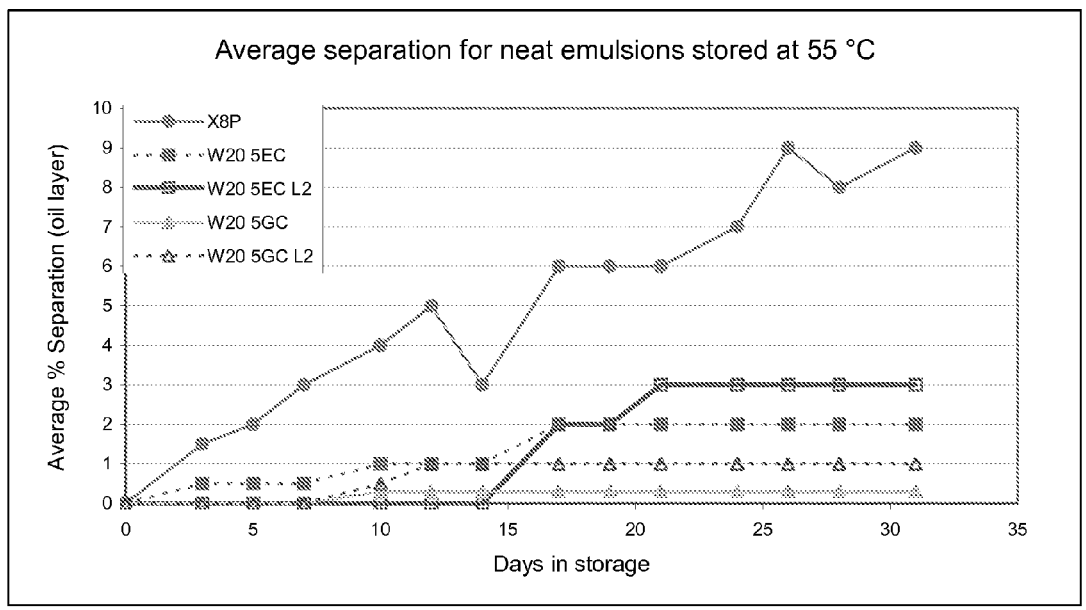
FIG. 1. Average separation of neat (100%) emulsions stored at 55° C.

Unless otherwise specified, "a" or "an" means "one or more". The present inventors discovered that compositions having emulsion particles with an average particle diameter of less than 250 nm ("small particle size nanoemulsion") have improved stability and/or activity. These small particle size nanoemulsions are useful in a wide range of applications for decreasing the infectivity, morbidity, and/or rate of mortality associated with a variety of pathogenic microorganisms. As used herein, the term "pathogenic microorganism" refers to a biological microorganism that is capable of producing an undesirable effect upon a host animal, and includes, for example, without limitation, bacteria, viruses, bacterial spores, molds, mildews, fungi, and the like. This includes all such biological microorganisms, regardless of their origin or of their method of production, and regardless of whether they exist in facilities, in munitions, weapons, or elsewhere.

Small particle size nanoemulsion compositions are useful, for example, as therapeutics for humans or animals, for decontaminating surfaces, individuals or locations colonized or otherwise infected by pathogenic microorganisms, for prophylaxis, treatment, and vaccine compositions, for decreasing the infectivity of pathogenic microorganisms in foodstuffs, and the like. The inactivation of a broad range of pathogenic microorganisms, including, for example, vegetative bacteria and enveloped viruses and bacterial spores, combined with low toxicity, make small particle size nanoemulsions well-suited for use as a general decontamination agent before a specific pathogen is identified.

A. Nanoemulsion Compositions

Particle size reduction to produce a small particle size nanoemulsion from a standard emulsion is efficiently and economically accomplished by high-pressure homogenizer or microfluidizer. Small particle size nanoemulsions can be rapidly produced in large quantities and are stable for many months at a broad range of temperatures.

An emulsion is a composition containing an aqueous phase and an oil phase. The term "emulsion" refers to, without limitation, any oil-in-water dispersions or droplets, including lipid structures that can form as a result of hydrophobic forces that drive apolar residues (e.g., long hydrocarbon chains) away from water and polar head groups toward water, when a water immiscible phase is mixed with an aqueous phase. These other lipid structures include, but are not limited to, unilamellar, paucilamellar, and multilamellar lipid vesicles, micelles, and lamellar phases. Classical or standard emulsions comprise lipid structures having an average particle size of greater than about 5 μm in diameter. Standard nanomulsions having smaller particle sizes are known, and comprise lipid structures having an average particle diameter of about 500 nm to about 5 μm. In one embodiment, a standard nanoemulsion has an average particle size of about As used herein, "small particle size nanoemulsions" refers to emulsions having an average particle diameters of less than or equal to about 250 nm. In one embodiment, average particle diameter is less than or equal to about 200 nm, less than or equal to about 150 nm, less than or equal to about 100 nm, or less than or equal to about 50 nm. As used herein, the term "nanoemulsion" can encompass both standard and small particle size nanoemulsions.

Emulsion particle size can be determined using any means known in the art, such as, for example, using laser light scattering.

A nanoemulsion composition contains about 5 to about 50 percent by volume (vol %) of aqueous phase. As used herein, percent by volume (vol %) is based on the total volume of an emulsion or small particle size nanoemulsion. In one embodiment, the aqueous phase is about 10 to about 40 vol %. In another embodiment, the aqueous phase is about 15 to about 30 vol %. The aqueous phase ranges from a pH of about 4 to about 10. In one embodiment the pH of the aqueous phase ranges from about 6 to about 8. The pH of the aqueous phase can be adjusted by addition of an acid or a base such as, for example, hydrochloric acid or sodium hydroxide. In one embodiment, the aqueous phase is deionized water (hereinafter "diH2O") or distilled water.

The oil phase of a nanoemulsion contains an oil and an organic solvent. The oil phase of a nanoemulsion contains about 30 to about 90 vol % oil, based on the total volume of the nanoemulsion. In one embodiment, the nanoemulsion contains about 60 to about 80 vol % oil. In another embodiment, the nanoemulsion contains about 60 to about 70 vol % oil. The oil phase also contains from about 3 to about 15 vol % of an organic solvent based on the total volume of the nanoemulsion. In one embodiment, the nanoemulsion contains about 5 to about 10 vol % of an organic solvent.

Suitable oils include, but are not limited to, soybean oil, avocado oil, squalene oil, olive oil, canola oil, corn oil, rapeseed oil, safflower oil, sunflower oil, fish oils, cinnamon bark, coconut oil, cottonseed oil, flaxseed oil, pine needle oil, silicon oil, mineral oil, essential oil, flavor oils, water insoluble vitamins, and combinations comprising one or more of the foregoing oils. In one embodiment, the oil is soybean oil.

Suitable organic solvents include, but are not limited to, organic phosphate solvents, alcohols, and combinations comprising one or more of the foregoing solvents. Suitable organic phosphate solvents include, but are not limited to, dialkyl and trialkyl phosphates having one to ten carbon atoms, more preferably two to eight carbon atoms. The alkyl groups of the di- or trialkyl phosphate can all the same or the alkyl groups can be different. In one embodiment, the trialkyl phosphate is tri-n-butyl phosphate. Without being held to theory, it is believed that organic solvents used in the small particle size nanoemulsions serve to stabilize the nanoemulsion and remove or disrupt the lipids in the membranes of pathogens.

Suitable alcohols include, for example, $C_1$-$C_{12}$ alcohols, diols, and triols, for example glycerol, methanol, ethanol, propanol, octanol, and combinations comprising one or more of the foregoing alcohols. In one embodiment, the alcohol is ethanol or glycerol, or a combinations thereof.

Small particle size nanoemulsion compositions can also contain one or more surfactants, present in the aqueous phase, the oil phase, or both phases of a nanoemulsion. While not limited to any particular proposed mechanism, a nanoemulsion composition may function to remove proteins from bacterial membranes, such that a surfactant that will "strip" a membrane of its proteins may be useful. A nanoemulsion can contain about 3 to about 15 vol % of surfactant, based on the total volume of nanoemulsion. In one embodiment, the nanoemulsion contains about 5 to about 10 vol % of surfactant.

Suitable surfactants include, but are not limited to, a variety of ionic and nonionic surfactants, as well as other emulsifiers capable of promoting the formation of nanoemulsions. Surfactants that allow the oil phase to remain suspended in the water phase can be used. In one embodiment, the nanoemulsion comprises a non-ionic surfactant such as a polysorbate surfactant, i.e., polyoxyethylene ether. Other useful surfactants include, but are not limited to, the polysorbate detergents sold under the tradenames TWEEN® 20, TWEEN® 40, TWEEN® 60, TWEEN® 80, phenoxypolyethoxyethanols and polymers thereof, such as Triton® (i.e., X-100, X-301, X-165, X-102, X-200), Poloxamer® 407, Spans (20, 40, 60, and 80), tyloxapol, and combinations comprising one or more of the foregoing surfactants. Additional appropriate surfactants include Brij®30, Brij®35, Brij®52, Brij®56, Brij®58, Brij®72, Brij®76, Brij®78, Brij®92, Brij®97, Brij®98, and Brij® 700. Anionic surfactants include, but are not limited to sodium dodecyl sulfate (SDS). Mixtures of surfactants are also contemplated. In one embodiment, the surfactant is TWEEN® 20 or Triton® X-100 or a combination thereof. Triton X-100 is a strong non-ionic detergent and dispersing agent widely used to extract lipids and proteins from biological structures. It also has virucidal effect against a broad spectrum of enveloped viruses. In another embodiment, the surfactant is nonoxynol-9.

Nanoemulsion compositions can further contain various additives. Exemplary additives include, for example, activity modulators, gelling agents, thickeners, auxiliary surfactants, other agents that augment cleaning and aesthetics, and combinations comprising at least one of the foregoing, so long as they do not significantly adversely affect the activity and/or stability of the emulsions. Additives can be incorporated into the nanoemulsion or formulated separately from the nanoemulsion, i.e., as a part of a composition containing a nanoemulsion.

"Activity modulators" are additives that affect the activity of a nanoemulsion against the target microorganism. Exemplary activity modulators are interaction enhancers such as germination enhancers, therapeutic agents, buffers, and the like, which are described below.

One class of activity modulators thus includes "interaction enhancers," compounds, or compositions that increase the interaction of the nanoemulsion with the cell wall of a bacterium (e.g., a Gram positive or a Gram negative bacteria) or a fungus, or with a virus envelope. Again, without being bound by theory, it is proposed that the activity of the emulsions is due, in part, to the interaction of a nanoemulsion with a microorganism membrane or envelope. Suitable interaction enhancers include compounds that increase the interaction of the nanoemulsion with the cell wall of Gram negative bacteria such as *Vibrio, Salmonella, Shigella, Pseudomonas, Escherichia, Klebsiella, Proteus, Enterobacter, Serratia, Moraxella, Legionella, Bordetella, Helicobacter, Haemophilus, Neisseria, Brucella, Yersinia, Pasteurella, Bacteiods*, and the like.

One exemplary interaction enhancer is a chelating agent. Suitable chelating agents include ethylenediaminetetraacetic acid (EDTA), ethylenebis(oxyethylenenitrilo)tetraacetic acid (EGTA), and combinations thereof. Chelating agents can be prepared in water or in a buffer, such as, for example, TRIS buffer. Chelating agents can be premixed with the aqueous phase or can be added to a diluent. Chelating agents can be used at a concentration of about 1 µM to about 50 mM, based on the total volume of the nanoemulsion composition. In one embodiment, the concentration of the chelating agent is between about 100 µM to about 50 mM. In a further embodiment, the concentration of chelating agent can be greater than or equal to about 25 µM, greater than or equal to about 50 µM, greater than or equal to about 70 µM greater than or equal to about 80 µM, greater than or equal to about 100 µM, greater than or equal to about 1 mM, or greater than or equal to about 2 mM. In an additional embodiment, the concentration of chelating agent can be less than or equal to about 40 mM, less than or equal to about 27 mM, less than or equal to about 25 mM, less than or equal to about 10 mM, or less than or equal to about 5 mM.

Another exemplary interaction enhancer is a cationic halogen-containing compound. A cationic halogen-containing compound can be premixed with the aqueous phase, or it may can be provided in combination with a nanoemulsion in a distinct formulation. A cationic halogen-containing compound can be used at a concentration of about 0.5 to about 7 vol. %, based on the total volume of the nanoemulsion. In one embodiment, a cationic halogen-containing compound can be used at a concentration of about 0.5 to about 3 vol. %, based on the total volume of the nanoemulsion.

Suitable cationic halogen-containing compounds include, but are not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, tetradecyltrimethylammonium halides, alkylbenzyldimethylammonium salts and combinations comprising one or more of the foregoing compounds. Suitable halides in the cationic halogen-containing compounds include chloride, fluoride, bromide and iodide. In one embodiment, the halide is chloride or bromide. In another embodiment the cationic halogen-containing compound is cetylpyridinium chloride or benzalkonium chloride or a combination thereof.

A "germination enhancer" enhances the germination of, for example, spores. Suitable germination enhancing agents include nucleosides, α-amino acids, salts and combinations thereof. Useful nucleosides include inosine. Useful α-amino acids include, for example, glycine and the L-enantiomers of alanine, valine, leucine, isoleucine, serine, threonine, lysine, phenylalanine, tyrosine, and the alkyl esters thereof. Suitable salts, include, for example, sodium chloride, ammonium chloride, magnesium chloride, calcium chloride, phosphate buffered saline (PBS), and potassium chloride. In one embodiment, the germination enhancer is a mixture of glucose, fructose, asparagine, sodium chloride, ammonium chloride, calcium chloride, and potassium chloride. In another embodiment, the germination enhancer is a combination containing L-alanine, inosine, PBS, and ammonium chloride.

Certain growth media contain germination enhancers and buffers. Thus, when testing nanoemulsions for their ability to inactivate spores, addition of germination enhancers may not be required, if the tests are conducted using media containing such germination enhancers. Similarly, the addition of certain growth media to emulsions can enhance sporicidal activity.

An effective amount of germination enhancer can be readily determined by one of ordinary skill in the art. Nucleosides and amino acids can be used in amounts of about 0.5 mM to about 100 mM. In one embodiment, nucleosides and amino acids are used at a concentration of about 1 mM to about 50 mM. In another embodiment, nucleosides and amino acids are used at a concentration of about 0.5 mM to about 5 mM. Salts can be present in amounts of about 0.5 mM to about 100 mM and PBS can be used at concentrations of about 0.05× to about 1×.

A germination enhancer can be incorporated into the aqueous phase prior to formation of the nanoemulsion. In one embodiment a germination enhancer is active at approximately neutral pH. In another embodiment, a germination enhancer can be active between pH of about 6 to about 8. Adjustment of pH of a nanoemulsion composition containing a germination enhancer can be achieved by any suitable means, such as, for example, dilution of a nanoemulsions in PBS or by preparations of a neutral nanoemulsion or by the addition of hydrochloric acid or sodium hydroxide.

"Therapeutic agent" refers to an agent that decreases the infectivity, morbidity, and/or rate of mortality associated with a pathogenic microorganism when administered to a subject affected by a pathogenic microorganism. Suitable therapeutic agents include, for example, antimicrobial agents, antiviral agents, antifungal agents, and the like, and combinations comprising one or more of the foregoing agents. There are many antimicrobial agents currently available for use in treating bacterial, fungal and viral infections. Generally, these agents include agents that inhibit cell wall synthesis (e.g., penicillins, cephalosporins, cycloserine, vancomycin, bacitracin), imidazole antifungal agents (e.g., miconazole, ketoconazole and clotrimazole), agents that act directly to disrupt the cell membrane of the microorganism (e.g., polymyxin and colistimethate and the antifungals nystatin and amphotericin B), agents that affect the ribosomal subunits to inhibit protein synthesis (e.g. chloramphenicol, the tetracyclines, erythromycin and clindamycin), agents that alter protein synthesis and lead to cell death (e.g. aminoglycosides), agents that affect nucleic acid metabolism (e.g. the rifamycins and the quinolones), antimetabolites (e.g., trimethoprim and sulfonamides), and the nucleic acid analogues (e.g. zidovudine, gangcyclovir, vidarabine, and acyclovir) which act to inhibit viral enzymes essential for DNA synthesis. Other useful therapeutic agents include, but are not limited to antimicrobials such as phenylphenol, propyl paraben and poly(hexamethylene biguanide) hydrochloride (PHMB).

Optionally, nanoemulsion compositions can be formed into gels by adding a gelling agent. Suitable gelling agents include, for example, hydrogels such as, for example, Natrosol® 250H NF (Hercules, Inc. Wilmington, Del.). A hydrogel can be added at concentration of about 0.5 wt % to about 5 wt %, based on the total volume of the gel. Other suitable gelling agents include, but are not limited to, about 0.05 wt % to about 3 wt % cellulose polymer, such as cellulose gum or cationic guar derivatives, and up to about 10 wt % petrolatum, glycerin, polyethylene glycol, incroquat behenyl TMS, cetyl palmitate, glycerol stearate, and the like.

A variety of auxiliary surfactants can optionally be used to enhance the properties of a nanoemulsion composition. The choice of auxiliary surfactant depends on the desire of the user with regard to the intended purpose of the composition and the commercial availability of the surfactant. In one embodiment, the auxiliary surfactant is an organic, water-soluble surfactant.

Other optional additives such as perfumes, brighteners, enzymes, colorants, detergent builders, suds suppressors, and the like can also be used in the compositions to enhance aesthetics and/or cleaning performance. Detergent builders sequester calcium and magnesium ions that might otherwise bind with and render less effective the auxiliary surfactants or co-surfactants. Detergent builders are particularly useful when auxiliary surfactants are used, and when the compositions are diluted prior to use with hard tap water, especially water having a hardness of, above about 12 grains/gallon.

A nanoemulsion composition can contain a suds suppressor. A suds suppressor is a low-foaming co-surfactant that prevents excessive sudsing during employment of the compositions on hard surfaces. Suds suppressors are also useful in formulations for no-rinse application of the composition. Concentrations of about 0.5 vol % to about 5 vol % are generally effective. Selection of a suds suppressor depends on its ability to formulate in a nanoemulsion composition and the residue as well as the cleaning profile of the composition. The suds suppressor should be chemically compatible with the components in a nanoemulsion composition and functional at the pH of a given composition. In one embodiment the suds suppressor or composition containing a suds suppressor does not leave a visible residue on surfaces on which a composition is applied.

Low-foaming co-surfactants can be used as a suds suppressor to mediate the suds profile in a nanoemulsion composition. Examples of suitable suds suppressors include block copolymers, alkylated primary and secondary alcohols, and silicone-based materials. Exemplary block co-polymers include, e.g., Pluronic® and Tetronic® (BASF Company). Alkylated alcohols include those which are ethoxylated and propoxylated, such as, tergitol (Union Carbide) or Poly-tergent® (Olin Corp.). Silicone-based materials include DSE (Dow Corning). The suds suppressors can be incorporated into the composition by any means known in the art.

B. Method of Making Small Particle Size Nanoemulsions

Small particle size nanoemulsions and compositions containing small particle size nanoemulsions can be produced by any suitable means. A small particle size nanoemulsion can be formed in the first instance or can be formed from a nanoemulsion having larger particles. For example, a small particle size nanoemulsion can be produced by reducing the particle size of a classical or standard nanoemulsion (hereinafter "standard nanoemulsion"), to produce a small particle size nanoemulsion wherein the average nanoemulsion particle size is less than about 250 nm. In other words, a nanoemulsion having an average particle diameter of greater than about 250 nm is treated in a manner effective to produce particles having an average diameter of less than or equal to about 250 nm. In one embodiment, small particle size nanoemulsion particles have an average diameter of less than or equal to about 200 nm, less than or equal to about 150 nm, less than or equal to about 100 nm, and less than or equal to about 50 nm.

Methods for the production of a standard nanoemulsion by mixing an oil phase with an aqueous phase are well-known. A nanoemulsion can be formed by blending an oil phase with an aqueous phase on a volume-to-volume basis ranging from about 1:9 to about 5:1, about 5:1 to about 3:1, or about 4:1, oil phase to aqueous phase. The oil and aqueous phases can be blended using an apparatus capable of producing shear forces sufficient to form a nanoemulsion such as, for example, a French press or a commercial low shear or high shear mixer. In one embodiment, the standard emulsions are prepared under conditions of high shear to produce a nanoemulsion having a substantially uniform particle size distribution. In one embodiment, a standard nanoemulsion for use in preparing a nanoemulsion composition is comprised of particles having an average diameter of about 500 nm to about 5 µm, about 500 nm to about 1 µm, 400 nm to about 5 µm, 400 nm to about 1 µm, from about 250 nm to about 5 µm, and from about 250 nm to about 1 µm. To obtain the desired pH, the pH of the aqueous phase can be adjusted using hydrochloric acid or sodium hydroxide.

Forming a small particle size nanoemulsion from a standard nanoemulsion can be accomplished, for example, by passing the standard nanoemulsion though a microfluidizer (Microfluidics Corp., Newton, Mass.) several times at a pressure sufficient to produce a desired particle size. A microfluidizer is a homogenizer that operates by pumping a fluid stream into an interaction chamber. The interaction chamber contains fixed-geometry microchannels that accelerate the fluid stream, resulting in high turbulence, shear, and cavitation. A H230Z (chamber 400 µm upstream of H210Z chamber (200 µm) can be used. Other chamber size and configurations (Y or Z) can be used in forming a nanoemulsion using a microfluidizer. During homogenization, a nanoemulsion can be circulated through a heat exchanger coil or otherwise cooled to keep the temperature of the nanoemulsion from increasing significantly. In one embodiment, a standard nanoemulsion is passed though the microfluidizer for two to five passes at a pressure of about 2,000 to about 10,000 psi. In another embodiment, the pressure is from 3,000 to about 4,000 pounds per square inch. These conditions can vary depending on factors such as standard nanoemulsion particle size, nanoemulsion composition, and desired final particle size Another means of forming a small particle size nanoemulsion is passage of a standard nanoemulsion through a high pressure homogenizer, like an EmulsiFlex® high pressure homogenizer (Avestin, Inc., Ottawa, Canada). The number of passages through the homogenizer as well as the flow rate will depend on the particle size of the standard nanoemulsion, nanoemulsion composition, and the desired particle size of the resulting small particle size nanoemulsion. Operating pressure is independent from flow rate and will remain at the set value over the process time. In one embodiment, the operating pressure is from about 2,500 to about 20,000 psi. As with the microfluidizing method discussed above, a nanoemulsion can be cooled using a heat exchanger or other method and the nanoemulsion can be passed though the homogenizer from about two to about five times. The particle size depends inversely on both the number of passages and on the operating pressure. See FIG. 5.

In addition to the above described methods, one can produce a small particle size nanoemulsion directly, without premixing. The direct use of, for example, either a microfluidizer or a high pressure homogenizer, as described above, can result in a small particle size nanoemulsion with the properties discussed above for a small particle size nanoemulsion produced from a premixed standard nanoemulsion.

Small particle size nanoemulsions can have a consistency ranging from a semi-solid cream to a watery liquid similar to skim milk. Creamy emulsions can be used as-is or mixed with water.

A nanoemulsion can be prepared in a diluted or an undiluted form. In one embodiment a nanoemulsion shows suitable stability in both diluted and undiluted forms. By suitable stability, it is meant that the emulsions do not show any signs of separation (oil phase from aqueous phase) for at least 6 months. In another embodiment a nanoemulsion does not show any sign of separation up to about 2 years. In a further embodiment, a nanoemulsion does not show any sign of separation for up to about 3 years. Settling of the diluted emulsions is an acceptable characteristic and does not indicate separation of an oil phase from an aqueous phase. Settling is due to separation of emulsions from its diluent, not an oil phase separating from an aqueous phase. Such settling is readily reversed by simple shaking of the nanoemulsion, while separation of the concentrated emulsions are not reversed by simple mixing, requiring instead re-emulsification.

The emulsions can also contain a first nanoemulsion emulsified within a second nanoemulsion, wherein the first and second emulsions can each contain an aqueous phase, an oil phase, and a surfactant. The oil phase of each of the first and second nanoemulsion can contain an oil and an organic solvent. The first and second nanoemulsion can be the same or different. A nanoemulsion can also contain a first nanoemulsion re-emulsified to form a second nanoemulsion.

One useful parameter for characterizing a nanoemulsion is "zeta potential." Zeta potential is the electrical potential of a shear plane (an imaginary surface separating a thin layer of liquid that shows elastic behavior) bound to a solid surface that shows normal viscous behavior. The stability of hydrophobic colloids depends, in part, on the zeta potential. Zeta potential of a nanoemulsion can be about −50 mV to about +50. In one embodiment, the zeta potential of the emulsions can be greater than or equal to about +10 mV. In another embodiment, the zeta potential is greater than or equal to about +20 mV. In a further embodiment, the zeta potential of the emulsions can be less than or equal to about +45 mV, less than or equal to about +40 mV or less than or equal to about +30 mV.

In one embodiment a nanoemulsion, comprising optional therapeutic agents, can be provided in the form of pharmaceutically acceptable compositions. The terms "pharmaceutically acceptable" or "pharmacologically acceptable" refer to compositions that do not produce significant adverse, allergic, or other untoward reactions when administered to an animal or a human Compositions for pharmaceutical use typically comprise a pharmaceutically acceptable carrier, for example, solvents, dispersion media, coatings, isotonic and absorption delaying agents and the like, and combinations comprising one or more of the foregoing carriers as described, for instance, in REMINGTON'S PHARMACEUTICAL SCIENCES, 15th Ed. Easton: Mack Publishing Co. pp. 1405-1412 and 1461-1487 (1975), and THE NATIONAL FORMULARY XIV 14th Ed., Washington: American Pharmaceutical Association (1975). Suitable carriers include, but are not limited to, calcium carbonate, carboxymethylcellulose, cellulose, citric acid, dextrate, dextrose, ethyl alcohol, glucose, hydroxymethylcellulose, lactose, magnesium stearate, maltodextrin, mannitol, microcrystalline cellulose, oleate, polyethylene glycols, potassium diphosphate, potassium phosphate, saccharose, sodium diphosphate, sodium phosphate, sorbitol, starch, stearic acid and its salts, sucrose, talc, vegetable oils, water, and combinations comprising one or more of the foregoing carriers. The use of such media and agents for pharmaceutically active substances is well known in the art. Except insofar as any conventional media or agent is incompatible with the emulsions of the present invention, their use in therapeutic compositions is contemplated. Supplementary active ingredients also can be incorporated into the compositions.

For topical applications, the pharmaceutically acceptable carriers can take the form of a liquid, cream, foam, lotion, or gel, and may additionally comprise organic solvents, emulsifiers, gelling agents, moisturizers, stabilizers, surfactants, wetting agents, preservatives, time release agents, and minor amounts of humectants, sequestering agents, dyes, perfumes, and other components commonly used in pharmaceutical compositions for topical administration.

C. Methods of Using Nanoemulsion Compositions to Inactivate a Pathogenic Microorganism Nanoemulsion compositions are particularly useful in applications where inactivation of pathogenic microorganisms is desired. The term inactivating means killing, eliminating, neutralizing, or reducing the capacity of a pathogenic microorganism to infect a host on contact. Nanoemulsion compositions are useful for decreasing the infectivity, morbidity, and/or rate of mortality associated with a variety of pathogenic microorganisms.

A method of inactivating a pathogenic microorganism comprises contacting the pathogenic microorganism with an amount a nanoemulsion composition which is effective to inactivate the microorganism. The step of contacting can involve contacting any substrate which may be or is suspected to be contaminated with a nanoemulsion composition. By substrate it is meant, without limitation any subject, such as a human or an animal (contact can be in vivo or ex vivo, any article, any surface, or any enclosure. A pathogenic microorganism can be, without limitation, a bacteria, a virus, a fungus, a protozoan or a combination thereof.

The step of contacting can be performed for any amount of time sufficient to inactivate a microorganism. In one embodiment, inactivation occurs within about 5 minutes to about 10 minutes after initial contact. However, it is understood that when the emulsions are used in a therapeutic context and applied topically or systemically, the inactivation may occur over a longer period of time, for example, 5, 10, 15, 20, 25 30, 60 minutes or longer after administration.

The step of contacting can be performed using any appropriate means of application. For example, compositions can be administered by spraying, fogging, misting, exposure to aerosols, wiping with a wet or saturated cloth or towlette, drenching, immersing.

Nanoemulsion compositions can be used to inactivate vegetative bacteria and bacterial spores upon contact. Bacteria inactivated by nanoemulsion compositions can be Gram negative or Gram positive bacteria. Gram negative bacteria include, for example and without limitation, *Vibrio, Salmonella, Shigella, Pseudomonas, Escherichia, Klebsiella, Proteus, Enterobacter, Serratia, Moraxella, Legionella, Bordetella, Gardnerella, Haemophilus, Neisseria, Brucella, Yersinia, Pasteurella, Bacteroids*, and *Helicobacter*. Gram positive bacteria include, for example, and without limitation, *Bacillus, Clostridium, Arthrobacter, Micrococcus, Staphylococcus, Streptococcus, Listeria, Corynebacteria, Planococcus, Mycobacterium, Nocardia, Rhodococcus*, and acid fast Bacilli such as *Mycobacterium*. In one embodiment, nanoemulsion compositions can be used to inactivate *Bacillus*, including, without limitation *B. anthracis, B. cereus, B. circulans, B. subtilis*, and *B. megaterium*. Nanoemulsion compositions can also be used to inactivate *Clostridium*, e.g., *C. botulinum, C. perfringens*, and *C. tetani*. Other bacteria that can be inactivated by a nanoemulsion include, but are not limited to, *H. influenzae, N. gonorrhoeae, S. agalactiae, S. pneumonia, S. pyogenes* and *V. cholerae* (classical and Eltor), and *Yersinia*, including, *Y. pestis, Y. enterocolitica*, and *Y. pseudotuberculosis*. In another embodiment, the bacteria is *B. anthracis*. In another embodiment, the bacteria is *Mycobaterium tuberculosis*.

Contacting a bacterial spore with a nanoemulsion inactivates the spore. Without being bound to any theory, it is proposed that the sporicidal ability of the nanoemulsions is by initiation of germination without complete reversion to the vegetative form, leaving the spore susceptible to disruption by the emulsions. Induction of germination using germination enhancers such as inosine and L-alanine can result in acceleration of the sporicidal activity of the nanoemulsion, while inhibition of initiation of germination with D-alanine can delay sporicidal activity. This unique action of a nanoemulsion, which can be better in efficiency than 1% bleach, is interesting because *Bacillus* spores are generally resistant to most disinfectants including many commonly used detergents. The sporicidal effect can start almost immediately. In one embodiment the sporicidal effect occurs within 30 minutes of contact with a nanoemulsion.

Contacting a nanoemulsion composition with a virus can inactivate a virus. The effect of nanoemulsion compositions on viral agents can be monitored using any suitable means, such as, for example, plaque reduction assay (PRA), cellular enzyme-linked immunosorbent assay (ELISA), P-galactosidase assay, and electron microscopy (EM). Viruses which can be inactivated by contact with a nanoemulsion composition include, without limitation, and virus of the families Baculoviridae, Herpesviridae, Iridoviridae, Poxyiridae, "African Swine Fever Viruses," Adenoviridae, Caulimoviridae, Myoviridae, Phycodnaviridae, Tectiviridae, Papovaviridae, Circoviridae, Parvoviridae, Hepadnaviridae, Cystoviridae, Birnaviridae, Reoviridae, Coronaviridae, Flaviviridae, Togaviridae, "Arterivirus," Astroviridae, Caliciviridae, Picornaviridae, Potyviridae, Retroviridae, Orthomyxoviridae, Filoviridae, Paramyxoviridae, Rhabdoviridae, Arenaviridae, and Bunyaviridae. In one embodiment, the virus is herpes, pox, papilloma, corona, influenza, hepatitis, sendai, sindbis and vaccinia viruses, west nile, hanta, and viruses which cause the common cold.

In yet another embodiment, contacting a nanoemulsion with a fungus inactivates the fungus. In one embodiment, the fungus is a yeast, such as, for example various species of *Candida* (e.g., *Candida albicans*) or filamentous yeast including but not limited to *Aspergillus* species or dermatophytes such as *Trichophyton rubrum, Trichophyton mentagrophytes, Microsporum canis, Microsporum gypseum*, and *Epiderophyton floccosum*, and types thereof, as well as others.

The methods and compositions, or components of the methods and compositions can be formulated in a single formulation, or can be separated into binary formulations for later mixing during use, as may be desired for a particular application. Such components can advantageously be placed in kits for use against microbial infections, decontaminating instruments and the like. Such kits may contain all of the essential materials and reagents required for the delivery of the formulations to the site of their intended action as well as any desired instructions.

For in vivo use, the methods and compositions may be formulated into a single or separate pharmaceutically acceptable syringeable composition. In this case, the container means may itself be an inhalant, syringe, pipette, eye dropper, or other like apparatus, from which the formulation may be applied to an infected area of the body, such as the lungs, injected into an animal, or even applied to and mixed with the other components of the kit.

A kit also can include a means for containing the vials in close confinement for commercial sale (e.g., injection or blow-molded plastic containers into which the desired vials are retained). Irrespective of the number or type of containers, the kits also may comprise, or be packaged with, an instrument for assisting with the injection/administration or placement of the ultimate complex composition within the body of an animal. Such an instrument may be an inhalant, syringe, pipette, forceps, measured spoon, eyedropper, or any such medically approved delivery vehicle.

Actual amounts of nanoemulsions and additives in the compositions can be varied so as to provide amounts effective to inactivate vegetative as well as sporular microorganisms and pathogens. Accordingly, the selected amounts will depend on the nature and site for treatment, the desired response, the desired duration of biocidal action, the condition of the subject being treated, and other factors. A nanoemulsion composition can comprise, for example, about 0.001% to about 100% nanoemulsion per milliliter of liquid composition. In one embodiment, a nanoemulsion composition can contain about 0.01% to about 90% nanoemulsion per milliliter of liquid. These are merely exemplary ranges. A nanoemulsion composition can also comprise greater than about 0.25%, about 1.0%, about 5%, about 10%, about 20%, about 35%, about 50%, about 65%, about 80%, about 90%, or about 95% of nanoemulsion per milliliter of liquid composition.

The small particle size nanoemulsions as described herein are more stable than standard emulsions under a variety of conditions, showing substantially no observable separation or settling for up to one month, preferably up to four months, more preferably up to or more than one year, up to about 21° C., preferably up to 40° C. Such stability is at no dilution, up to 2.5% dilution, up to 10% dilution, more preferably up to 50% dilution or higher.

The small particle size nanoemulsions perform equal to or better than standard emulsions in inactivating a pathogenic microorganism, exhibiting a less than 10% failure rate, preferably a less than 5% failure rate, more preferably a less than 1% failure rate, and most preferably a 0% failure rate against pathogens. The invention is further illustrated by the following non-limiting examples.

1. Prevention and Treatment of Infection

Nanoemulsion compositions are useful for the prevention and treatment of infection. A method of inactivating a pathogenic microorganism comprises contacting a subject infected with or suspected to be infected with the microorganism with a nanoemulsion composition comprising an aqueous phase, an oil phase, and one or more surfactants. The oil phase comprises an oil and an organic solvent, as discussed above. The nanoemulsion particles have an average diameter of less than or equal to about 250 nm. In one embodiment, the particles have an average diameter of less than or equal to about 200 nm, less than or equal to about 150 nm, less than or equal to about 100 nm, or less than or equal to about 50 nm.

The pathogenic microorganism may have systemically infected the subject or on the surface of the subject. Where the microorganism is not on the subject, the is delivered to the site of infection by any suitable method, for example injection, oral administration, suppositories, and the like. In one embodiment the subject is an animal. In a further embodiment, the animal is a human.

Exemplary infected states that can be treated or prevented with nanoemulsions include, but are not limited to, bacterial, fungal, protozoal, and/or viral vaginal infection, sexually transmitted diseases (STDs), skin infections such as, acne, impetigo, athlete's foot, onychomycosis, candidiasis and other acute fungal infections, herpes simplex and zoster and infections associated with psoriasis or other skin inflammatory diseases. In one embodiment, an infected state is particularly susceptible to topical treatment. As used herein, "infected states" is inclusive of contamination with pathogenic microorganisms, and treatment and prevention of such infected states includes, but is not limited to, wound decontamination, decontamination of skin, airways, and/or mucosal surfaces (e.g., with anthrax spores, viruses, bacteria, and/or fungi); and the like. Nanoemulsion compositions can also be used as a surgical irrigant. The emulsions can be used in the personal health care industry in deodorants, soaps, body wash, acne/dermatophyte treatment agents, treatments for halitosis, and skin disinfecting.

Nanoemulsions can be used in a variety of combination therapies, particularly those directed to microorganisms. This approach is often advantageous in avoiding the problems encountered as a result of multidrug resistance, for example.

In one embodiment, a nanoemulsion can be used in the prevention or treatment of genital infections. Such sexually transmitted genital infections include, but are not limited to genital herpes, human papilloma virus (HPV), human immunodeficiency virus (HIV), trichomoniasis, gonorrhea, syphilis, and chlamydia. A nanoemulsion can be applied to the genitals either before or after sexual intercourse or both before and after sexual intercourse. In one embodiment, a nanoemulsion is introduced into the vagina of a female, at about the time of sexual. In another embodiment, a nanoemulsion is introduced into the vagina of a female prior to intercourse. A nanoemulsion can also be administered to other mucous membranes. Application of a nanoemulsion composition to genitalia can be accomplished using any appropriate means including, for example, ointments, jellies, inserts (suppositories, sponges, and the like), foams, and douches.

A nanoemulsion can also be used in the treatment of non-sexually transmitted genital infections, such as fungal, protozoan, bacterial infections. Fungal infections treatable with a nanoemulsion include, but are not limited, to tinea, *candida* (e.g., *Candida albicans*). Nonsexually treated bacterial infections treatable with a nanoemulation include, but are not limited, nonspecific vaginitis and bacterial vaginitis caused by, for example, *Gardnerella vaginalis, Gardneralla mobiluncus*, and *Mycoplasma hominis*.

Nanoemulsion compositions can also be used for the prevention and treatment of respiratory infection. Nanoemulsion compositions can be used to prevent infection by, without limitation, the common cold, influenza, tuberculosis, legionnaire's disease, and acute respiratory syndrome (SARS). In one embodiment, a nanoemulsion composition is applied to the respiratory passages using, for example, a nasal spray, such that the spray coats the respiratory passages before exposure to these pathogens. In another embodiment, this use can substantially inactivate or eliminate a respiratory pathogen preventing the pathogen from inducing a pathogenic response. The use of a nanoemulsion in the prevention and treatment of a respiratory infection can also stimulate an immunological response against a specific pathogen which can protect from further exposure to the same pathogen.

2. Immunogenic Compositions and Vaccine Applications:

A nanoemulsion can be mixed with a microorganism, a recombinant antigen, or a combination thereof to yield an immunogenic composition. The concentration of microorganism can range from approximately $10^2$ to approximately $10^{10}$. The concentration of antigen can range from approximately 1 μg to approximately 1 mg, either alone or mixed with other adjuvants which include but are not limited to CpG oligonucleotides. As used herein "immunogenic composition" refers to any composition capable of eliciting an immune response. In one embodiment, the immune response results in production of protective antibodies.

An immunogenic nanoemulsion composition can be administered topically on the skin or on mucosal membranes of a subject. Administration of an immunogenic composition can be performed using any appropriate means and using any appropriate formulation known in the art.

In one embodiment, a nanoemulsion composition contains substantially inactivated B. anthracis. In one embodiment, a nanoemulsion composition contains a peptide comprising at least a portion of anthrax protective antigen (PA). PA is known to provide protection against infection in conventional vaccines. A vaccine can also contain an attenuated strain of B. anthracis. In one embodiment, PA is isolated from B. anthracis extract. In another embodiment, PA is recombinant PA. B. anthracis PA concentration can range from about 1 μg to about 1 mg. In one embodiment, B. anthracis PA concentration ranged from between about 2.3 μg to about 30 μg.

In another embodiment, a nanoemulsion contains substantially inactivated vaccinia for use as can be used as a small pox vaccination. In a further embodiment, a nanoemulsion. In a further embodiment, a nanoemulsion can be used to create a vaccine against influenza virus. In an additional embodiment, a vaccine composition can contain an inactivated influenza virus or a portion thereof.

A nanoemulsion composition can contain substantially inactivated Mycobateria tuberculosis or a portion thereof. In one embodiment, the Mycobateria tuberculosis-containing nanoemulsion composition is efficacious as a vaccine against tuberculosis.

A nanoemulsion composition can contain substantially inactivated hepatitis virus or an portion thereof. In one embodiment, the hepatitis-containing nanoemulsion is efficacious as a vaccine against hepatitis infection. In another embodiment, the hepatitis virus is hepatitis A, hepatitis B, or hepatitis C, or a mixture thereof. In a further embodiment, the hepatitis virus is hepatitis B.

A nanoemulsion composition can contain substantially inactivated HIV or a portion thereof. In one embodiment, the HIV-containing nanoemulsion is efficacious as a vaccine against HIV infection.

A nanoemulsion composition can be applied to mucosa to prevent infection by a microorganism both as a prophylaxis and as a broad spectrum immunogenic composition. This administration results in a broad spectrum prophylactic immunogenic composition which can both prevent infection by a pathogenic microorganism and also cause an immune response against a pathogenic microorganism which comes in contact with the nanoemulsion-coated mucosa of a subject. In one embodiment, this immunogenic response can provide protection or future protection to the subject against a microorganism. In another embodiment, the microorganism causes influenza, tuberculosis, the common cold, SARS or other respiratory diseases.

In one embodiment, a nanoemulsion composition can be administered prior to contact with microorganisms. Upon contact with a pathogenic microorganism, the microorganism is inactivated. The nanoemulsion-inactivated microorganism can stimulate an immune response in a subject. In other words, a nanoemulsion composition can inactivate a microorganism and also function an as an adjuvant to aid in stimulating an immune response against the microorganism or its antigens. In one embodiment, the immune response results in antibodies capable of neutralizing a microorganism and thus providing immunological protection of the subject against the microorganism. Examples of microorganisms which can be used in conjunction with a nanomemulsion include, but are not limited to bacteria, bacterial spores, viruses, protozoa, and fungi.

3. Decontamination of Medical Devices

Nanoemulsion compositions are useful for decontaminating surfaces colonized or otherwise infected by pathogenic microorganisms. These applications include, for example, disinfecting or sterilizing medical devices, contact lenses and the like, particularly when the devices or lenses are intended to be used in contact with a patient or wearer. As used herein "medical devices" includes any material or device that is used on, in, or through a patient's body in the course of medical treatment, whether prophylactic or therapeutic treatment. Medical devices include, but are not limited to, such items as implants, for example urinary catheters, intravascular catheters, dialysis shunts, wound drain tubes, skin sutures, vascular grafts, implantable meshes, intraocular devices, heart valves, and the like; wound care devices, for example wound dressings, surgical sutures, biologic graft materials, tape closures and dressings, surgical incise drapes, and the like; drug delivery devices, for example skin patches, mucosal patches and medical sponges; and body cavity and personal protection devices, for example tampons, sponges, surgical and examination gloves, toothbrushes, birth control devices such as IUD's and IUD strings, diaphragms and condoms; and the like.

For applications of this type, the compositions may be conveniently provided in the form of a liquid or foam, and may be provided with emulsifiers, surfactants, buffering agents, wetting agents, preservatives, and other components commonly found in compositions of this type. The nanoemulsion compositions can be impregnated into absorptive materials, such as sutures, bandages, and gauze, or coated onto the surface of solid phase materials, such as staples, zippers, and catheters to deliver the compositions to a site for the prevention or therapy.

4. Sterilization and Disinfectant Applications

The present invention is also useful for disinfection and sterilization for medical, hospital, ambulance, institutional, educational, agricultural, food processing, and industrial applications.

In one embodiment, a nanoemulsion composition can be used to prevent contamination, disinfect or sterilize other surfaces, including surfaces used in the food industry, for example equipment and areas where food is processed, packaged and stored; vehicles; machinery; household surfaces, and other surfaces. For example, a nanoemulsion composition can be used to eliminate contamination in meat processing plants, particularly of microorganisms such as *Listeria monocytogenes, Salmonellae* species and *Escherichia* species by cleaning slaughterhouses or food packaging facilities on a continual basis with the composition. In addition, nanoemulsion compositions can be formulated into sprays for hospital, food processing and serving facilities, and household uses such as cleaning and disinfecting patient rooms, household appliances, kitchen and bath surfaces, and the like.

When used in liquid form to decontaminate surfaces, the emulsions can be admixed with an aqueous carrier liquid. The aqueous carrier liquid is preferably not toxic and is chemically compatible with the inventive emulsions. The aqueous carrier liquid can comprise solvents commonly used in hard surface cleaning compositions. Such solvents are preferably chemically stable at the pH of the emulsions, have good filming/residue properties, and are miscible with water. Preferred carrier liquids comprise water or a miscible mixture of a $C_2$-$C_4$ alcohol and water. The alcohol or glycerol can be used to adjust the viscosity of the compositions Preferably, the aqueous carrier liquid is water or a water-ethanol mixture containing from about 0 to about 50% ethanol or other solvents. Alternatively, when used to clean hard surfaces, the emulsions may be in the form of a gel, foam, or cream, preferably a gel, and may be provided with emulsifiers, surfactants, buffering agents, wetting agents, preservatives, and other components commonly found in compositions of this type.

A nanoemulsion can also be used for mold remediation for building, equipment, and facilities. Examples of molds include, but are not limited to *Cladosporium, Fusarium, Alternaria, Curvularia, Aspergillus*, and *Penicillium*.

A nanoemulsion composition can also be used in the food industry in preventing and treating food contaminated with pathogens. Thus, such compositions may be used to reduce or inhibit microbial growth or otherwise abrogate the deleterious effects of microbial contamination of food. For example, a nanoemulsion composition can be used to kill bacteria and fungus on poultry eggs, fruit, vegetables, and meat. Also, the inclusion of a nanoemulsion compositions within the food product itself would be effective in killing bacteria that may have been accidentally contaminated meat or poultry. A nanoemulsion composition can be included in juice products to prevent growth of certain fungi, which cause contamination and lead to production of mycotoxins. For these applications, the nanoemulsion compositions are applied in food industry acceptable forms such as washes, dips, additives, preservatives, or seasonings. The use of media and agents for additives, preservatives, and seasonings that are acceptable in food industry is well known in the art. Except insofar as any conventional additives, preservatives and seasonings are incompatible with the emulsions, their use in preventing or treating food born microbes and their toxic products is contemplated. Supplementary active ingredients may also be incorporated into the compositions.

5. Biodefense Applications

Nanoemulsion compositions are also useful for biodefense applications, such as, for example, decontamination of a building, surface, garment, and personnel, and disinfection or sterilization of soil and/or waterways contaminated with a pathogenic microorganism, for example as a result of a biological warfare attack.

Nanoemulsion compositions can be delivered and applied for detoxification and decontamination using any appropriate means. Such decontamination procedures are well known to those of skill in the art and may involve simple application of the formulation in the form of a liquid spray or may require a more rigorous regimen. For example, nanoemulsion compositions can be applied by, without limitation, spraying, fogging, misting, exposure to aerosols, wiping with a wet or saturated cloth or towlette for personal skin decontamination; drenching, immersing, spraying with a hand-held spray bottle or backpack-mounted spray apparatus, showering, spraying with a curtain spray, pouring, dripping, and bathing in the liquid formulation. Additionally, a nanoemulsion can be deployed in a semi-solid carrier, such as in gels, lotions, creams, and pastes. Deployment can be accomplished by people, deployed from aircraft, helicopters, trucks, tanks, railroad, boats, bicycle, or by automated systems, including mobile robots.

Deployment can include applying the formulation to a surface inside of an industrial setting selected from, for example, a food processing plant, a hospital, an agricultural facility, an institutional building, an ambulance, and a cooking area.

A fog (e.g., aerosols with particulate sizes ranging from 1-30 μm) can be used to achieve effective decontamination in areas where decontamination by a foam would be difficult, if not impossible. One example is the interior of air conditioning ducts. A fog can be generated at registers and other openings in the duct and travel a significant distance inside of the duct to decontaminate hard to reach places. A relatively automated fog-based decontamination system can be set-up at the scene of an attack. Remotely activated foggers can be placed inside of a facility and turned on at periodic intervals (from a remote location) to completely decontaminate the facility. This method greatly decreases the potential for decontamination personnel to be exposed to a biological warfare agent.

A nanoemulsion can be used to decontaminate wounds contaminated with or suspected to be contaminated with bacteria, bacterial spores, virus, fungus, protazoa or combinations thereof. In one embodiment the bacteria is *B. anthracis*. In another embodiment, the virus is smallpox. In a further embodiment, the bacteria is a *Yersinia* species.

A nanoemulsion can also be used to decontaminate skin contaminated with or suspected to be contaminated with bacteria, bacterial spores, virus, fungus, protazoa or combinations thereof. In one embodiment the bacteria is *B. anthracis*. In another embodiment, the virus is smallpox. In a further embodiment the bacteria is *Yersinia* species.

A nanoemulsion is also useful for prophylaxis treatment of skin against bacteria, bacterial spores, virus, fungus, protazoa, or combinations thereof. In one embodiment the bacteria is *B. anthracis*. In a further embodiment, the bacterial spore is cutaneous *B. anthracis* spore. In another embodiment, the virus is smallpox. In a further embodiment, the bacteria is *Yersinia* species.

A nanoemulsion is also useful for battlefield prophylaxis treatment of mucosa against bacteria, bacterial spores, virus, fungus, protazoa or combinations thereof. In one embodiment the bacteria is *B. anthracis*. In a further embodiment, the bacterial spore is *B. anthracis* spore. In another embodiment, the virus is smallpox. In a further embodiment, the bacteria is *Yersinia* species. In one embodiment, nanoemuslions can be applied intranasally prior to and/or immediately after suspected contamination by bacteria, bacterial spores, virus, fungus, or combinations thereof.

A nanoemulsion composition is also useful for decontamination of surfaces contaminated by or suspected to be contaminated by bacteria, bacterial spores, virus, fungus, protazoa or combinations thereof as the result of, for example, a biological warfare attack. In one embodiment the bacteria is *B. anthracis*. In a further embodiment, the bacterial spore is *B. anthracis* spore. In another embodiment, the virus is smallpox. In a further embodiment, the bacteria is *Yersinia* species. In one embodiment, a nanoemulsion composition can be applied prior to and/or immediately after suspected contamination by bacteria, bacterial spores, virus, fungus, or combinations thereof. In a further embodiment, the nanoemulsion composition is applied intranasally. Nanoemulsion can be applied to surfaces using any appropriate means. In one embodiment, a nanoemulsion is delivered as a spray, liquid, fog, foam, or aerosol to contaminated or suspected contaminated surfaces.

A nanoemulsion composition is also useful for decontamination buildings contaminated by or suspected to be contaminated by bacteria, bacterial spores, virus, fungus, or combinations thereof. In one embodiment the bacteria is *B. anthracis*. In a further embodiment, the bacterial spore is *B. anthracis* spore. In another embodiment, the virus is smallpox. In a further embodiment, the virus is *Yersinia* species. In one embodiment, nanoemuslions can be applied intranasally prior to and/or immediately after suspected contamination by bacteria, bacterial spores, virus, fungus, or combinations thereof. Nanoemulsion can be applied to surfaces using any appropriate means. In one embodiment, a nanoemulsion is delivered as a spray, liquid, fog, foam, or aerosol to contaminated or suspected contaminated surfaces.

EXAMPLE 1

Comparison of Standard Emulsions and Small Particle Size Nanoemulsions

The nanoemulsions are described by the components of the nanoemulsion according to Table 1. Unless otherwise noted, the oil is soybean oil. In the formulations, the detergent is listed first, followed by the volume percentage of the detergent (e.g., $W_{20}5$ refers to 5 vol % of Tween 20). In the formulations, the designation L2 refers to a small particle size nanoemulsion produced by a microfluidizer, while the absence of the L2 designation refers to a standard nanoemulsion (i.e., average particle sizes of 250 nm to about 1 micrometer). The designation L3 refers to nanoemulsions produced using an Avesting high pressure homogenizer.

TABLE 1

| Component | Symbol |
| --- | --- |
| Tween 20 | $W_{20}$ |
| Ethanol | E |
| Cetylpyridinium chloride | C |
| EDTA | ED |
| Triton X-100 | X |
| Tributyl phosphate | P |
| Glycerol | G |
| Benzalkonium chloride | BA |

A first nanoemulsion is produced from a mixture containing 548 milliliters of water, 2.24 grams of EDTA, 25 grams of cetylpyridiunium chloride, 125 milliliters of Tween 20, 200 milliliters of ethanol and 1600 milliliters of soybean oil. The first nanoemulsion is pre-mixed with a Silverson L4RT mixer and a fine emulsifier screen for 10 minutes at 10,000±500 revolutions per minute.

The first nanoemulsion is then processed in a Microfluidics M-110EH microfluidizer processor using an H210Z (200 μm) chamber downstream of an H230Z (400 μm) chamber. The first nanoemulsion is passed through the microfluidizer 3 to 4 times at a pressure of 3,500±500 pounds per square inch (psi) using cooling ice in the tray surrounding the chambers. The small particle size nanoemulsion produced is referred to as $W_{20}$EC ED L2.

The second nanoemulsion is then diluted with distilled water to produce a series of diluted nanoemulsions. The water and the nanoemulsion can be mixed by shaking, for example, until the nanoemulsion is incorporated into the water. Exemplary diluted nanoemulsions are as shown in Table 2. The percentage shown refers to the volume percentage of the nanoemulsion in the dilution.

TABLE 2

| Formulation | water | $W_{20}5EC$ ED L2 |
| --- | --- | --- |
| 50% $W_{20}5EC$ ED L2 | 500 mL | 500 mL |
| 20% $W_{20}5EC$ ED L2 | 800 mL | 200 mL |
| 10% $W_{20}5EC$ ED L2 | 900 mL | 100 mL |
| 5% $W_{20}5EC$ ED L2 | 950 mL | 50 mL |
| 2.5% $W_{20}5EC$ ED L2 | 975 mL | 25 mL |

EXAMPLE 2

Method of Making a Small Particle Size Nanoemulsion

A standard nanoemulsion (i.e., particles sizes of 250 nm to 5 micrometers) is formed as follows. A mixture of 22 vol % distilled water, 1 wt/vol % cetylpyridinium chloride, 5 vol % Tween 20, 64 vol % soybean oil, and 8 vol % ethanol based on the total volume of the mixture is formed. The nanoemulsion is formed by mixing for 5 minutes at 10,000±500 revolutions per minute with a Silverson L4RT mixer with a standard mixing assembly and a fine emulsion screen. The standard nanoemulsion is denoted as $W_{20}5EC$.

A small particle size nanoemulsion is formed by passing the $W_{20}5EC$ nanoemulsion 4 times through a Microfluidics M-110EH microfluidizer processor using an H210Z (200 μm) chamber downstream of an H230Z (400 μm) chamber. The small particle size nanoemulsion is denoted as $W_{20}5EC$ L2.

After formation, the $W_{20}5EC$ and $W_{20}5EC$ L2 emulsions are diluted with water for further testing. Particle sizes are determined by Particle Sizing Systems (PSS) Nicomp Model 380. The samples are diluted 1/2000 in distilled water to measure the particle size. The formulations and data are shown in Table 3.

TABLE 3

| Formulation No. | Formulation | Amount of nanoemulsion | Amount of water | Average Particle Size, nm |
| --- | --- | --- | --- | --- |
| 1 | $W_{20}5EC$ | — | — | 421.4 |
| 2 | 50% $W_{20}5EC$ | 90 mL | 90 mL | 454 |
| 3 | 20% $W_{20}5EC$ | 36 mL | 144 mL | 437.5 |
| 4 | 10% $W_{20}5EC$ | 18 mL | 162 mL | 418.8 |
| 5 | 5% $W_{20}5EC$ | 9 mL | 171 mL | 427.4 |
| 6 | 2.5% $W_{20}5EC$ | 4.5 mL | 175.5 mL | 470.3 |
| 7 | $W_{20}5EC$ L2 | — | — | 152 |
| 8 | 50% $W_{20}5EC$ L2 | 90 mL | 90 mL | 99.3, 219.5* |
| 9 | 20% $W_{20}5EC$ L2 | 36 mL | 144 mL | 144.2 |
| 10 | 10% $W_{20}5EC$ L2 | 18 mL | 162 mL | 153 |
| 11 | 5% $W_{20}5EC$ L2 | 9 mL | 171 mL | 177.8 |
| 12 | 2.5% $W_{20}5EC$ L2 | 4.5 mL | 175.5 mL | 157.7 |

*When there is wide range of particle sizes (Nicomp reading), two methods of calculation are used As shown in Table 3, dilution of the emulsions does not appreciably affect the particle size of either the standard nanoemulsion or the small particle size nanoemulsion. The average particle size for the $W_{20}5EC$ emulsions is about 400 to about 500 nm (samples 1-6) and for the $W_{20}5EC$ L2 emulsions is about 140 to about 220 nm (samples 7-12).

EXAMPLE 3

Effect of Microfluidizer Chamber Size on the Size of Small Particle Size Nanoemulsion Particles A $W_{20}5G$ BA2 nanoemulsion is passed through different combinations of microfluidizer chambers as shown in Table 4. The $W_{20}5G$ BA2 L2 small particle size nanoemulsion is made with 1 pass with a Silverson L4RT mixer and 4 passes through a microfluidizer. Combinations of chamber having 75, 200, 400 micrometer microchannels are used to determine the relationship between the size of the microchannels and the size of the particles produced.

TABLE 4

| Sample | First chamber, µm | Second chamber, µm | Particle size, nm |
|---|---|---|---|
| 1 | 75 | 100 | 174 |
| 2 | 100 | 75 | 165 |
| 3 | 75 | 200 | 185 |
| 4 | 200 | 75 | 180 |
| 5 | 75 | 400 | 211 |
| 6 | 400 | 75 | 199 |

As shown in Table 4, the chamber size utilized in the microfluidizer, when varied between 75 and 400 µm, does not significantly affect the particle size of the emulsions. In all cases, the particle size is less than or equal to about 250 nm.

EXAMPLE 4

Effect of Number of Passes Through the Microfluidizer on Emulsion Particle Size

A $W_{20}5G$ BA2 nanoemulsion is formed using either a Silverson L4RT mixer (high shear) or a household hand mixer (low shear). The nanoemulsion is then passed through the microfluidizer for 1 to 6 passes and the particle size measured. The relationship between the number of passes in the microfluidizer and the particle size of the emulsions are shown in Table 5 and FIG. 5.

TABLE 5

| Sample | Type of First Mixer | Number of Passes Through Microfluidizer | Nanoemulsion Particle Size (nm) (three independent experiments with different emulsion lots) |
|---|---|---|---|
| 1 | High shear | 1 | 183, 221, 267 |
| 2 | High shear | 2 | 183, 205, 195 |
| 3 | High shear | 3 | 210, 202, 201 |
| 4 | High shear | 4 | 155, 156, 156 |
| 5 | High shear | 4 | 220, 157, 180 |
| 6 | High shear | 5 | 157, 132, 158 |
| 7 | High shear | 6 | 196, 161, 168 |
| 8 | Low shear | 0 | 426, 529, 522 |
| 9 | Low shear | 1 | 275, 210, 205 |
| 10 | Low shear | 2 | 218, 168, 218 |
| 11 | Low shear | 3 | 183, 151, 129 |
| 12 | Low shear | 4 | 182, 179, 180 |

Figure 5:
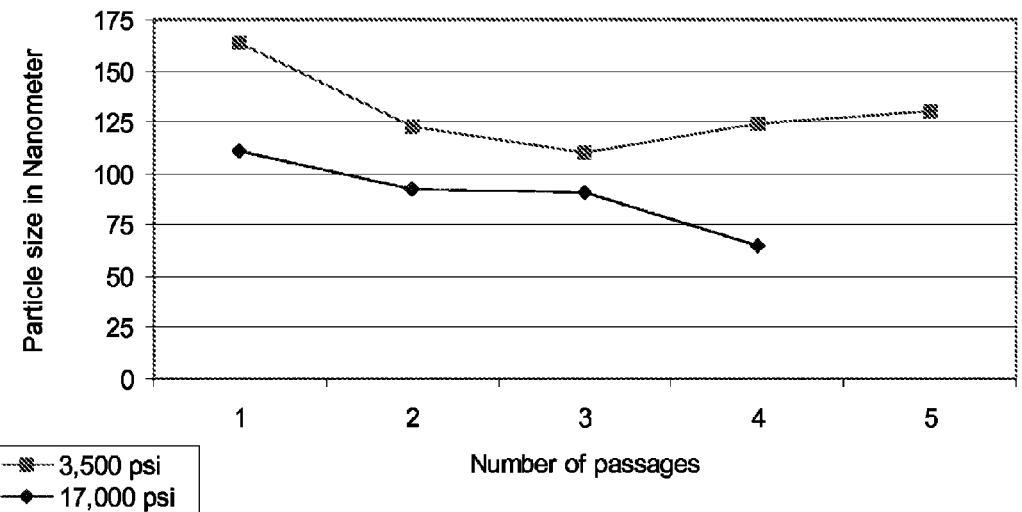
FIG. 5. Dependence of nanoemulsion particle size of passage number and pressure in Avestin EmulsiFlex® C3.

As shown in Table 5 and FIG. 5, the number of passes through the microfluidizer does not have a large effect on the nanoemulsion particle size. As shown in Sample 4 and 5, 4 passes through the microfluidizer produces particle sizes consistently below 250 nm. Regarding high shear versus low shear mixing of the starting emulsion, while high shear mixing can produce a more consistent particle size distribution than the low shear mixing, high shear mixing of the starting emulsion is not required to produce the small particle size nanoemulsions.

EXAMPLE 5

Combined Effects of Number of Passes Through the Microfluidizer and Microfluidizer Chamber Size The effect of both the number of passes through the microfluidizer and the chamber size in the microfluidizer are studied for different formulations. The starting emulsions are prepared using either a Silverson L4RT mixer ("Silv") or a Ross HSM-410X high shear mixer with a 3 inch X-series rotor/stator pre-set to a 0.010 gap (Ross) in order to determine the effect of mixing method on the particle size of the starting nanoemulsion (i.e., prior to passage through the microfluidizer). The L2 emulsions are produced by passing a standard nanoemulsion produced by Silverson mixing through a microfluidizer. The particle sizes are shown in Table 6.

TABLE 6

| Sample | Formulation | High shear Mixer type | Interactive chamber used | Number of passages | Particle size, nm |
|---|---|---|---|---|---|
| 1 | Nanowash + alcohol* | Silv | — | — | 410-486 |
| 2 | $W_{20}5G$ BA2 | Silv, 5 minutes mixing | — | — | 304-371 |
| 3 | $W_{20}5G$ BA2 | Silv, 20 min mixing | — | — | 283-340 |
| 4 | S8G | Silv | — | — | 350 |
| 5 | $W_{20}5EC$ | Silv | — | — | 381 |
| 6 | $W_{20}5G$ | Silv | — | — | 486 |
| 7 | $W_{20}5G$ BA2 | Ross | — | 1 | 260 |
| 8 | $W_{20}5G$ BA2 | Ross | — | 2 | 247 |
| 9 | $W_{20}5G$ BA2 | Ross | — | 3 | 281 |
| 10 | $W_{20}5G$ BA2 | Ross | — | 4 | 229-254 |
| 11 | $W_{20}5G$ BA2 | Microfluidizer | 400, 200 | 2 | 196 |
| 12 | $W_{20}5G$ BA2 | Microfluidizer | 400, 200 | 3 | 195 |
| 13 | $W_{20}5G$ BA2 | Microfluidizer | 200, 200 | 3 | 173 |
| 14 | $W_{20}5G$ BA2 | Microfluidizer | 75, 200 | 3 | 210 |
| 15 | $W_{20}5G$ BA2 | Microfluidizer | 75, 200 | 3 | 235 |
| 16 | $W_{20}5G$ BA2 | Microfluidizer | 200, 400 then diluted using 75, 200 | 3 | 179 |
| 17 | S8G** | Microfluidizer | 75, 200 | 3 | 161 |
| 18 | $W_{20}5EC$ | Microfluidizer | 75, 200 | 3 | 178 |
| 19 | $W_{20}5EC$ | Microfluidizer | 75, 200 | 3 | 158 |
| 20 | $W_{20}5G$ | Microfluidizer | 75, 200 | 3 | 223 |
| 21 | $W_{20}5GC$*** | Microfluidizer | 400, 200 | 3 | 189, 200, 225, 226 |
| 22 | $X_8GC$ | Microfluidizer | 400, 200 | 3 | 130, 145 |
| 23 | $X_8E_6G_2$**** | Microfluidizer | 400, 200 | 3 | 249 |

*1% $W_{20}5$ GBA2 + 2 mM EDTA + 20% ethanol
**8% SDS, 6% glycerol, 64% soybean oil, 20% water
***5% Tween 20, 8% glycerol, 1% cetylpyridinium chloride, 64% soybean oil, 22% water
****8% Triton X100, 6% ethanol, 2% glycerol, 64% soybean oil, 20% water As shown in Table 6, the Silverson high shear mixer (samples 1-6) produces particle sizes of about 300 nm to about 500 nm. The Ross high shear mixer (Samples 7-10) produces particle sizes of 260 nm after 1 pass to about 229 to 254 nm after 4 passes. The Ross high shear mixer is thus capable of producing smaller particle sizes than the Silverson mixer. Also shown in Table 6 is that the samples passed through the microfluidizer (samples 11-23) have smaller particle sizes than the samples mixed with either high shear mixer (samples 1-10).

Regarding the samples passed through the microfluidizer, as shown in samples 11 and 12, similar particle sizes are obtained with either 2 or 3 passes through the microfluidizer. Samples 13-16 show that changing the microchannel size of the microfluidizer chamber does not decrease the particle size of the emulsions. Samples 17-23 illustrate that, independent of the formulation of the emulsions, emulsions having particle sizes of less than about 250 nm can be formed by passing the emulsions through a microfluidizer.

EXAMPLE 6

Particle Sizes and Zeta Potentials for Different Nanoemulsion Formulation

In this experiment, the particle sizes and zeta potentials for different small particle size nanoemulsion formulations are determined. The emulsions are formed by passing a starting nanoemulsion through the microfluidizer for 3 passes using the H230Z+H210Z chambers. The particle size and zeta potential are measured by Nicomp 380 Particle sizer. The data are shown in Table 7.

TABLE 7

| Sample | Formulation | Particle Size | Zeta (mV) |
|---|---|---|---|
| 1 | 1% $W_{20}5G$ BA2 L2 + 2 mM EDTA | 186 | 11 |
| 2 | $W_{20}5G$ BA2 L2 in water | 183 | 27 |
| 3 | $W_{20}5GC$ L2 | 168-236 | 30-33 |
| 4 | $W_{20}5G$ SA2 OA2 L2* | 226 | 33 |
| 5 | $W_{20}5E$ SA3 L2 | 154 | 31 |
| 6 | $W_{20}5E$ SA3 L2 + 2 mM EDTA | 131 | 12 |
| 7 | $W_{20}5G$ SA3 L2** | 215 | 32 |
| 8 | $W_{20}5G$ SA3 L2 + 2 mM EDTA | 187, 191 | 12 |
| 9 | $W_{20}5E$ L2 | 189 | −25 |
| 10 | $W_{20}5EC$ L2, premixed | 156, 182 | 31 |
| 11 | $W_{20}5EC$ L2 | 146 | 41 |

*5% Tween 20, 8% glycerol, 2% sterylamine, 2% oleyl alcohol, 61% soybean oil, 21% water
**5% Tween 20, 8% glycerol, 3% Sterylamine, 61% Soybean oil, 23% water As shown in Table 7, all of the formulations have particle sizes of less than or equal to about 250 nm.

EXAMPLE 7

Stability of Nanoemulsions

A $W_{20}5EC$ nanoemulsion was formed containing 5% Tween-20, 8% ethanol, 1% cetylpyridinium chloride, 64% soybean oil, and the balance water. A $W_{20}5EC$ L2 nanoemulsion is formed using 2 passes on a microfluidizer. A $W_{20}5GC$ nanoemulsion is formed containing 5% Tween-20, 8% glycerol, 1% cetylpyridinium chloride, 64% soybean oil, and the balance water. A $W_{20}5GC$ L2 nanoemulsion is formed using 2 passes on a microfluidizer. An X8P nanoemulsion is formed using 8% Triton X-100, 8% tributyl phosphate, and the balance water.

Stability is determined by evaluating the physical appearance of the emulsions. As used herein, creaming is the presence of a white layer of creamy material on top of the nanoemulsion that is more opaque than the rest of the nanoemulsion. Settling is a gradual decrease in opacity of the nanoemulsion from top to bottom due to separation of the more dense diluent (water) at the bottom from the less dense nanoemulsion at the top. The water appears as transparent layer at the bottom of the vial. Settling is classified as follows: Mild settling: the nanoemulsion appears cloudy with a gradient of "cloudiness" where it gets more opaque as you go upwards. Moderate settling: a partially clear aqueous solution appears on the bottom of the sample. The rest of the nanoemulsion appears cloudy with a gradient of cloudiness getting more opaque as you go up. Some creaming may be on the surface. Severe settling: nanoemulsion has the appearance of three distinct layers, a partially clear bottom, cloudy middle, and creamy top. Extreme settling: only two layers, a thick partially clear bottom and a thin creamy top.

Separation is the phase separation of the nanoemulsion ingredients. Separation is classified as follows: Mild separation: the surface of the nanoemulsion shows few visible oil droplets. Moderate separation: the surface of the nanoemulsion has a film of oil. The bottom of the nanoemulsion may have a clear aqueous layer. Severe separation: nanoemulsion has the appearance of three distinct layers, a clear aqueous layer on the bottom, a white or cloudy middle layer and a dense oily layer on the top. Extreme separation: total separation into an oil layer on top and water on bottom.

The ambient storage stability test includes storing the neat emulsions in polypropylene bottles or centrifuge tubes at room temperature (22-25° C.). Containers may be mixed or opened during the observation period. The emulsions are observed for separation or any other changes in appearance. The observation period is varied due to different manufacturing dates of the emulsions. The data for $W_{20}5EC$ emulsions are shown in Table 8.

TABLE 8

| Sample | Days in storage | Bottle fullness | Type of container | Appearance |
|---|---|---|---|---|
| 1 | 579 | ¼ | 125 ml PP | severe separation 93%: <7% nanoemulsion between oil & water |
| 2 | 619 | ¼ | 125 ml PP | extreme separation |
| 3 | 505 | ⅔ | 250 ml PP | moderate separation - 6% oil |
| 4 | 585 | ⅔ | 250 ml PP | moderate separation - 8% oil |
| 5 | 457 | ⅔ | 250 ml PP | mild separation - 1% oil |
| 6 | 497 | ⅔ | 250 ml PP | moderate separation - 1.5% oil |
| 7 | 184 | full | 125 ml PP | mild-oil drop in air space |
| 8 | 224 | full | 125 ml PP | mild-oil drop in air space |
| 9 | 184 | ¾ | 125 ml PP | mild separation -1% oil film |
| 10 | 224 | ¾ | 125 ml PP | moderate separation - 2% oil film |
| 11 | 184 | ⅔ | 125 ml PP | mild separation - 4% oil |
| 12 | 224 | ⅔ | 125 ml PP | moderate separation - 6% oil |
| 13 | 112 | ¼ | 500 ml PP | intact |
| 14 | 152 | ¼ | 500 ml PP | moderate separation - 3% oil |
| 15 | 33 | full | 30 ml PP | intact |
| 16 | 74 | full | 30 ml PP | mild separation - 1 of 4 vials with oil film |
| 17 | 74 | ½ | 250 ml PP | mild separation |

*PP = polypropylene

The data for $W_{20}5EC$ L2 emulsions are shown in Table 9.

TABLE 9

| Sample | Days in storage | Bottle fullness | Type of container | Appearance |
|---|---|---|---|---|
| 18 | 116 | full | 30 ml PP | intact |
| 19 | 157 | full | 30 ml PP | intact |
| 20 | 74 | ¼ | 60 ml PP | intact |
| 21 | 115 | ¼ | 60 ml PP | intact |
| 22 | 75 | full | 500 ml PP | intact |
| 23 | 115 | full | 500 ml PP | intact |
| 24 | 33 | full | 30 ml PP | intact |
| 25 | 74 | full | 30 ml PP | intact |

As shown in Tables 8 and 9, the small particle size nanoemulsions are more stable at room temperature than comparable standard emulsions. Batches of standard $W_{20}5EC$ neat nanoemulsion stored at ambient temperatures longer than 5 months show oil forming a film or layer on the surface of the nanoemulsion. The thickness of the oil layer is variable and may be related in part to the amount of air in the storage container in addition to the number of times the container has been entered.

Batches of smaller particle size $W_{20}5EC$ L2 neat nanoemulsion are stored at ambient temperatures for up to 4 months. No settling or separation is observed in these batches.

Accelerated stability testing is also performed as follows. Glass vials are filled with 20 milliliters of neat, 10% diluted and 2.5% diluted nanoemulsion. The emulsions are stored at 55° C. and observed 3 times a week for changes in physical appearance. One additional set of vials for the $W_{20}5EC$ L2 emulsions is filled completely (about 25 milliliters) to eliminate air during storage. These full vials are inverted at day 7 to facilitate observation of creaming and separation.

Neat emulsions (100%) of standard $W_{20}5EC$ and small particle size nanoemulsion $W_{20}5EC$ L2 under accelerated stability testing at 55° C. show a film of oil separating after 4 and 5 days, respectively (FIG. 1 and Table 10).

TABLE 10

| Nanoemulsion | Average Days to Mild or Moderate Separation | | | Average Days to Severe or Extreme Separation | | |
| --- | --- | --- | --- | --- | --- | --- |
| | Neat | 10% | 2.50% | Neat | 10% | 2.50% |
| X8P | 3 | N | N | 10 | N | N |
| $W_{20}5EC$ | 4.3 | N | N | N | N | N |
| $W_{20}5EC$ L2 | 5.3 | N | N | N | N | N |
| $W_{20}5EC$ L2 full* | N | N | N | N | N | N |
| $W_{20}5GC$ | 5.7 | N | N | N | N | N |
| $W_{20}5GC$ L2 | 8.7 | N | N | N | N | N |

N = No separation

For comparison, the X8P neat nanoemulsion shows signs of instability with a distinct clear aqueous layer on the bottom and a 5% oil layer on the surface. Neat emulsions of both $W_{20}5GC$ and $W_{20}5GC$ L2 show yellowing of the oil film on the surface of the nanoemulsion, whereas for $W_{20}5EC$ and $W_{20}5EC$ L2, the oil film is colorless. The neat small particle size nanoemulsions are stable for 1-3 days longer than the standard emulsions.

No diluted nanoemulsion (10% or 2.5%) shows separation of oil after 4 weeks observation at 55° C. (Table 10).

Table 11 shows the settling observed for the nanoemulsions after accelerated aging.

TABLE 11

| Nanoemulsion | Average Days to Mild or Moderate Settling | | | Average Days to Severe or Extreme Settling | | |
| --- | --- | --- | --- | --- | --- | --- |
| | Neat | 10% | 2.50% | Neat | 10% | 2.50% |
| X8P | N | 3 | 3 | N | 10 | 10 |
| $W_{20}5EC$ | N | 3 | 3 | N | 19 | 10 |
| $W_{20}5EC$ L2 | N | 10.6 | 5 | N | N | N |
| $W_{20}5EC$ L2 full* | N | N | 5 | N | N | N |
| $W_{20}5GC$ | N | 5 | 3 | N | 26 | 19 |
| $W_{20}5GC$ L2 | N | 10 | 3 | N | N | N |

On average, the small particle size nanoemulsions exhibit less oil separation and less separation of the oil and water layers than the standard emulsions (Table 10). The small particle size nanoemulsions exhibit comparable settling and creaming to the standard emulsions when undiluted and improved stability when diluted to 10% or 2.5% (Table 11).

Figure 2:
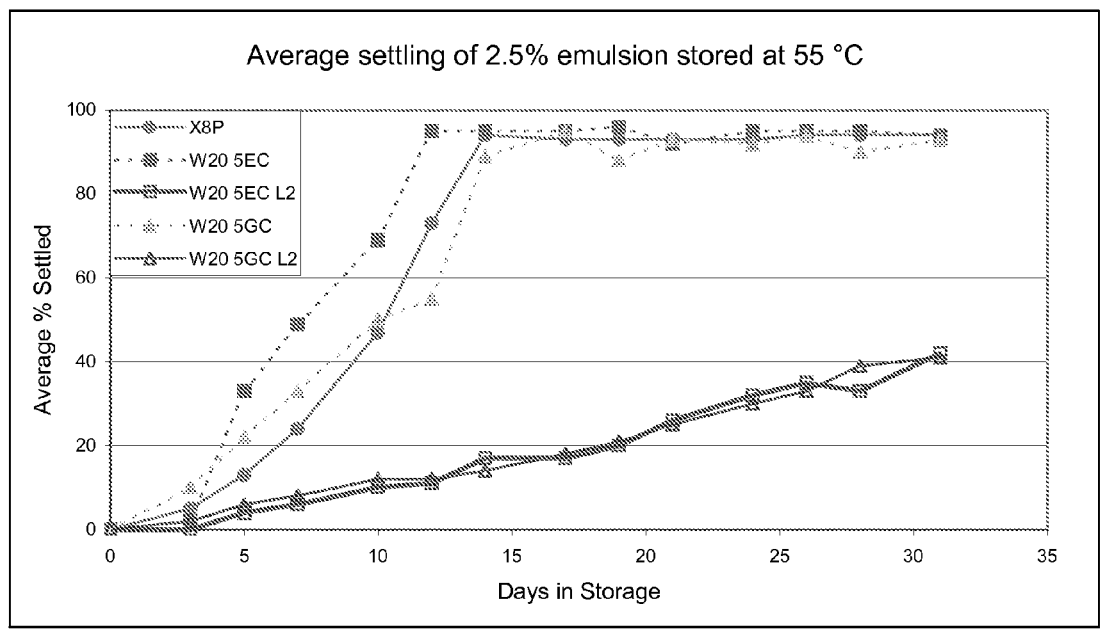
FIG. 2. Average settling of 10% emulsions stored at 55° C.
Figure 3:
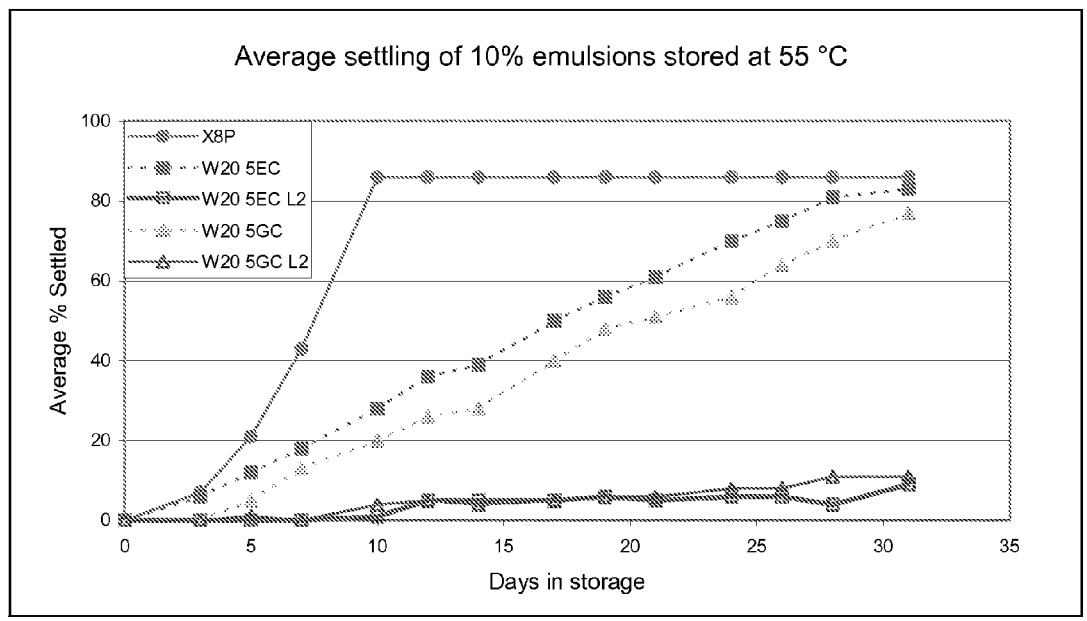
FIG. 3. Average settling of 2.5% emulsions stored at 55° C.

Settling and creaming are more pronounced in the diluted large particle size emulsions compared to the diluted emulsions stored at 55° C. (FIGS. 2-3, Table 12). The 10% $W_{20}5EC$ nanoemulsion is 83% settled after 4 weeks, whereas the 10% $W_{20}5EC$ L2 nanoemulsion is only 9% settled. The onset of settling occurred later in the smaller particle size nanoemulsion, within 10 days for 10% $W_{20}5EC$ L2 compared to only 3 days for 10% $W_{20}5EC$. Table 12 shows the creaming and settling of the emulsions.

Table 12 shows the separation and settling of emulsions under accelerated aging conditions

TABLE 12

| Nanoemulsion | Separation | | Settling | | | |
| --- | --- | --- | --- | --- | --- | --- |
| | Neat Oil | Water | 10% Cream | Settling | 2.50% Cream | Settling |
| X8P | 9 | 17 | 13 | 86 | 6 | 94 |
| $W_{20}5EC$ | 2 | 0 | 14 | 83 | 5 | 94 |
| $W_{20}5EC$ L2 | 3 | 0 | 2 | 9 | 2 | 42 |
| $W_{20}5EC$ L2 full* | 0 | 0 | 2 | <14 | 2 | 28 |
| $W_{20}5GC$ | 0.3** | 0 | 13 | 77 | 5 | 93 |
| $W_{20}5GC$ L2 | 0.7** | 0 | 0 | 11 | 2 | 41 |

The $W_{20}$ 5EC L2 nanoemulsion that is stored in vials that are completely full show no separation and less settling compared to the same nanoemulsion stored in vials containing an air space (Table 12). Interestingly, the bottom breaks off at the seam at day 10 and day 21 for 2 of the full vials of diluted nanoemulsion.

Figure 4:
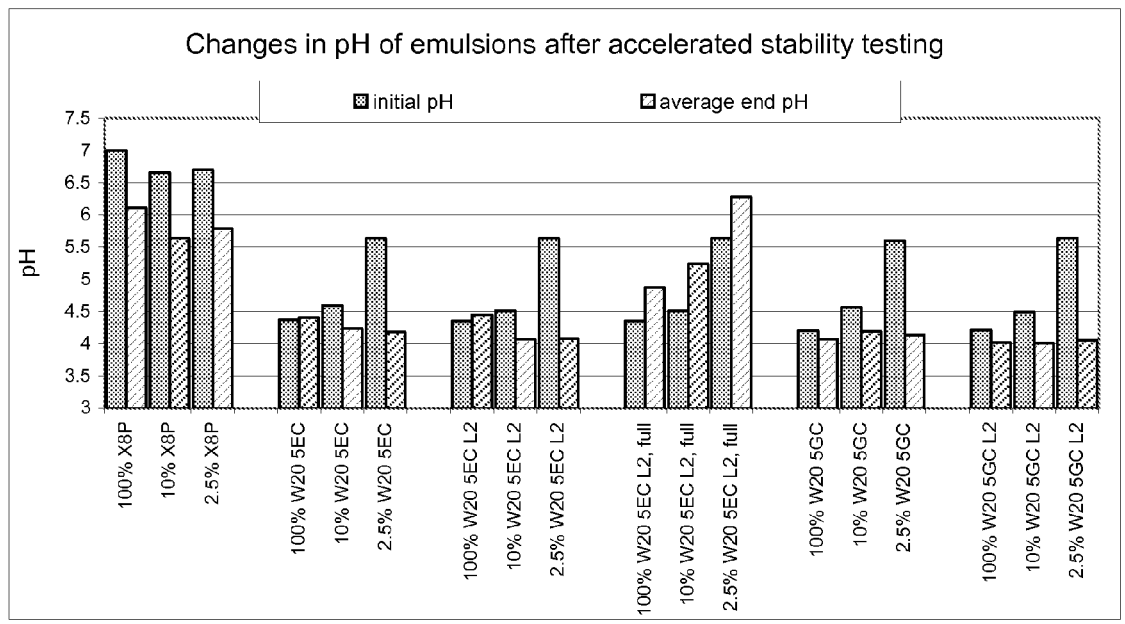
FIG. 4. Change in pH after accelerated stability testing. pH of neat and diluted emulsions is measured on day 0 and after 31 days incubation at 55° C.

The change in pH after accelerated stability testing is measured. The pH of each nanoemulsion is measured at the beginning and at the end of the accelerated stability incubation at 55° C. Diluted emulsions are measured using a 3-in-1 combination electrode and neat emulsions are measured with a semi-micro electrode. The initial pH of the neat $W_{20}5EC$, and $W_{20}5EC$ L2, $W_{20}5GC$, and $W_{20}5GC$ L2 emulsions is similar for each nanoemulsion, ranging from 4.2-4.4. The pH increases with increasing dilution of these nanoemulsion to a pH of 5.6 for the 2.5% dilutions. After 4 weeks at 55° C., the pH of the neat emulsions remains unchanged, whereas the pH of the diluted emulsions decreases to a value similar to that of the neat nanoemulsion, (4.0-4.4). In contrast, $W_{20}5EC$ L2 incubated in vials that are filled completely, slightly increased in pH after 4 weeks incubation at 55° C. The difference between the neat and diluted nanoemulsion is also maintained (FIG. 4).

Additional stress testing is preformed by centrifugation, freezing and autoclaving. In the centrifugation test, neat (100%) and a 10% dilution of $W_{20}5EC$ L2 nanoemulsion are centrifuged at 1,650×g for 30 minutes at room temperature, then stored at room temperature for observation. An additional sample of the 10% dilution of $W_{20}5EC$ L2 is not centrifuged and is stored at room temperature for comparison. After storage at room temperature for 6 weeks, no separation of neat or diluted emulsions is observed. Only slight creaming is seen in the 10% diluted emulsions with no difference between the centrifuged and uncentrifuged sample.

In the freezing test at −18° C. neat nanoemulsion and a 10% dilution of $W_{20}5EC$ L2 are placed at −18° C. for 24 hours, and then left at room temperature for observation. The neat nanoemulsion $W_{20}5EC$ L2 is frozen at −18° C. for 24 hours then thawed and observed. After 24 hours at room temperature no separation is observed in the neat or 10% diluted nanoemulsion. Creaming is observed in the 10% diluted nanoemulsion and no settling were noted.

In the autoclaving test neat $W_{20}5EC$, $W_{20}5EC$ L2, $W_{20}5GC$, and $W_{20}5GC$ L2 emulsions are placed in a Yamato autoclave for 15 minutes at 121° C., and then stored at room temperature for observation. Both emulsions containing ethanol ($W_{20}5EC$ and $W_{20}5EC$ L2) boiled over in the autoclave and severe separation is observed immediately after autoclaving. The emulsions containing glycerol are intact after autoclaving and displayed no separation up to 3 days when stored at room temperature.

EXAMPLE 8

Manufacture of Small Particle Size Nanoemulsions Using a High Pressure Homogenizer This example demonstrates using a high pressure homogenizer (Avestin Emulsiflex C3) to reduce the particle size of a standard nanoemulsion to particles having a diameter of 50-150 nm. The size of the nanoemulsion particles depends on the pressure and number of passages.

First, a standard nanoemulsion containing particles having an average diameter of 250 nm to 5 micrometers, preferably about 300 nanometer to 1 micrometer is formed. The standard nanoemulsion contains 22 vol % distilled water, 1 wt/vol % cetylpyridinium chloride, 5 vol % Tween 20, 64 vol % soybean oil, 8 vol % ethanol and 2 mM EDTA, based on the total volume of the mixture formed. The nanoemulsion is formed by mixing for 5 minutes at 10,000±500 revolutions per minute with a Silverson L4RT mixer with a standard mixing assembly and a fine emulsion screen. The standard nanoemulsion is denoted as $W_{20}5EC\ ED$.

Small particle size nanoemulsions containing particles of various sizes are then formed by passing the standard nanoemulsion through an Avestin EmulsiFlex under different pressures ranging from 3,500-17,000 psi. The nanoemulsion was passed between 4-5 times under the same conditions. The machine applies high pressure to push the nanoemulsion through a dynamic homogenizing valve. Table 13 describes the different nanoemulsion particle size resulting from different passages into the emulsifier.

TABLE 13

| Name | Passages in the high pressure emulsifier | Pressure (psi) | Particle size (nm) |
|---|---|---|---|
| $W_{20}5EC\ ED$ | None | — | 277 |
| $W_{20}5EC\ ED\ L3$ | 1 | 17,000 | 111 |
| $W_{20}5EC\ ED\ L3$ | 2 | 17,000 | 92 |
| $W_{20}5EC\ ED\ L3$ | 3 | 17,000 | 91 |
| $W_{20}5EC\ ED\ L3$ | 4 | 17,000 | 65 |
| $W_{20}5EC\ ED\ L3$ | 1 | 3,500 | 164 |
| $W_{20}5EC\ ED\ L3$ | 2 | 3,500 | 123 |
| $W_{20}5EC\ ED\ L3$ | 3 | 3,500 | 110 |
| $W_{20}5EC\ ED\ L3$ | 4 | 3,500 | 124 |
| $W_{20}5EC\ ED\ L3$ | 5 | 3,500 | 130 |

Table 13 and FIG. 5 demonstrate that particle size is inversely dependent on the amount of pressure applied during homogenization as well as the number of passages to which the nanoemulsion is subjected.

EXAMPLE 9

Testing of Disinfectants Containing the Nanoemulsions

Example 9 compares the efficacy of a standard nanoemulsion versus a small particle size nanoemulsion (denoted L2) as a disinfectant.

The AOAC (Association of Official Analytical Chemist) dilution test is a carrier-based test. Carriers (i.e., stainless steel cylinders) are inoculated with a test microorganism, dried, exposed to a dilution of a disinfectant product, and cultured to assess the survival of the bacteria. A single test involves the evaluation of 60 inoculated carriers contaminated with one microorganism against one product sample. In addition to the 60 carriers, 6 carriers are required to estimate carrier bacterial load and 6 more are included as extras. Thus, a total of 72 seeded carriers are required to perform a single test.

A contaminated dried cylinder carrier is added to the medication tubes. Immediately after placing carrier in medication tube, tubes are swirled 3 times before placing tube into bath. Ten minutes after each carrier is deposited into the disinfectant, each carrier is removed from the medication tube with a sterile hook, tapped against the interior sides of the tube to remove the excess disinfectant, and transferred into the primary subculture tube containing the appropriate neutralizer (Letheen broth, 10 mL in 20×150 mm tubes). The subculture tubes are swirled for 3-4 seconds. Transfer into the primary subculture tubes should be within ±5 seconds of the actual time of transfer (10 minutes). The bacterial carrier load on at least 2 carriers is assayed.

After a minimum of 30 minutes from when the test carrier was deposited, each carrier is transferred using a sterile wire hook to a second subculture tube containing 10 mL of the appropriate neutralizer. The carriers are transferred in order, but the intervals do not have to be timed. The tubes are swirled for 3-4 seconds and the subcultures incubated at 37° C. for 48 hours. If the broth culture appears turbid, the result is positive. A negative result is one in which the broth appears clear. Each tube is shaken prior to recording results to determine the presence or absence of turbidity. The primary and secondary subculture tubes for each carrier represent a "carrier set." A positive result in either the primary or secondary subculture tube is considered a positive result for a carrier set.

Gram stains are performed on smears taken from the positive culture tubes. For additional confirmatory tests, a loop of broth is streaked on the selective media appropriate for the test microorganism and incubated for 24 hours at 37° C.

Table 14. Gram staining and culture on selective media required to ensure the identity of the microorganism.

TABLE 14

| | S. choleraesuis | S. aureus | P. aeruginosa |
|---|---|---|---|
| Gram stain | Gram negative rods | Gram positive cocci arranged in clusters | Gram negative rods |
| Selective media | MacConkey agar | Mannitol salt agar | Pseudosel agar |
| Morphology on selective media | Pale large colonies, agar turning light color. | Circular, small, fluorescent yellow colonies. | Circular, small, initially opaque, turning fluorescent green over time. |
| Regular media | TSA* | TSA | TSA |

*Tryptic soy agar

Table 15 show the results for a $W_{20}5G\ BA2+2$ mM EDTA at pH 7.2 nanoemulsion and a $W_{20}5G\ BA2\ L2+2$ mM EDTA at pH 7.2 nanoemulsion with *Staphylococcus aureus*.

TABLE 15

| Sample | Formulation | Carriers failed | Total tested | Number of experiments | Percentage failed |
|---|---|---|---|---|---|
| 1 | 1% $W_{20}5G\ BA2$ + 2 mM EDTA | 16 | 304 | 6 | 5.26% |

TABLE 15-continued

| Sample | Formulation | Carriers failed | Total tested | Number of experiments | Percentage failed |
|---|---|---|---|---|---|
| 2 | 1% $W_{20}$5G BA2 L2 + 2 mM EDTA | 2 | 240 | 4 | 0.83% |
| 3 | 1% $W_{20}$5G BA2 L2 | 1 | 300 | 6 | 0.33% |

As shown in Table 15, a disinfectant made with the small particle size nanoemulsions has a lower failure ratio than a standard nanoemulsion. The standard nanoemulsion has a failure rate of about 5%. The small particle size nanoemulsions have a failure rate of less than 1%.

Table 16 also shows results obtained for various formulations exposed to *Staphylococcus aureus*.

TABLE 16

| Sample | Formulation | Number of Experiments | No. of Failed Cylinders | Percentage failed |
|---|---|---|---|---|
| 1 | 1% $W_{20}$5G BA2 + 2 mM EDTA pH 7.2 | 6 | 304 | 5.3% |
| 2 | 1% $W_{20}$5G BA2 + 2 mM EDTA pH 8.0 | 9 | 272 | 11.4% |
| 3 | 1% $W_{20}$5G BA2 L2 + 2 mM EDTA pH 7.2 | 4 | 240 | 0.83% |
| 4 | 1% $W_{20}$5G BA2 pH 7.2 | 6 | 300 | 0.33% |

Table 16 demonstrates that the small particle size nanoemulsions (Samples 3 and 4) show greater efficacy against *Staphylococcus aureus* than the standard emulsions (Samples 1 and 2).

Table 17 shows the results obtained for various formulations exposed to *Salmonella choleraesuis*.

TABLE 17

| Sample | Formulation | Number of Experiments | No. of Cylinders tested | Percentage failed |
|---|---|---|---|---|
| 1 | 1% $W_{20}$5G BA2 + 2 mM EDTA pH 7.2 | 2 | 120 | 0% |
| 2 | 1% $W_{20}$5G BA2 + 2 mM EDTA pH 8.0 | 1 | 30 | 0% |
| 3 | 1% $W_{20}$5G BA2 L2 + 2 mM EDTA pH 7.2 | 1 | 60 | 0% |
| 4 | 1% $W_{20}$5G BA2 ($L_2$) pH 7.2 | 60 | 240 | 0% |

Table 17 demonstrates that the small particle size nanoemulsions (Samples 3 and 4) show similar efficacy against *Salmonella choleraesuis* compared to the standard emulsions (Samples 1 and 2). Overall in the disinfectant test, the small particle size nanoemulsions perform as well as or better than the standard emulsions.

EXAMPLE 10

Bactericidal Properties of the Nanoemulsions Against *Staphylococcus aureus*

The bactericidal activity of the nanoemulsions is tested using a tube rotation test. In this test, first a culture is prepared by picking one colony from the stock culture plate of *Staphylococcus aureus*, streaking fresh TSA and incubating overnight at 37° C. The next morning, one colony is picked from the agar plate and transferred into 25 mL of TSB in a 50 mL screw-cap tube and incubated at 37° C. on a tube rotator for 4-5 hours until the culture becomes turbid. Bacteria grown for 4-6 hours is added to 10 mL TSB until the culture media becomes slightly turbid.

$W_{20}$5EC and $W_{20}$5EC L2 are used as previously described. The emulsions are then diluted to 2%, 1%, 0.2%, 0.1%, and 0.02% by volume with water.

Bactericidal testing is performed as follows. In 1.7 mL microfuge tubes, 0.5 mL cell suspension and 0.5 mL of each of the nanoemulsion dilutions is mixed and the tubes capped. A positive control containing 0.5 mL of cell suspension and 0.5 mL of sterile distilled water is prepared in parallel. The tubes are incubated on a tube rotator at 37° C. for 10 minutes. Each of the preparations is serially diluted (5 log diluation) in a 96-well plate using PBS. 25 µL from each dilution on is incubated on TSA at 37° C. overnight. The colonies on the control and test plates are counted. The count on the control plate provides the initial bacterial count. The initial bacteria count is provided as:

Initial bacterial count=CFU×40×plate dilution where CFU is the colony forming units per mL. The colonies on each of the test plates is counted. Plates having between 20-50 CFU are counted. The report log reduction is provided as:

Report Log reduction=Log(count on the control treatment)−Log(count on the treatment).

Small particle size nanoemulsions have several advantages over standard emulsions. First, the small particle size nanoemulsions can be more stable than the standard emulsions when stored at room temperature or at 55° C. The small particle size nanoemulsions are capable of resisting separation or settling when stored at room temperature for four months. The undiluted small particle size nanoemulsions can take about 1 to 3 days longer to exhibit moderate separation than the standard emulsions. The 2.5% to 10% diluted small particle size nanoemulsions can take about 2 to 7 days longer to exhibit moderate to extreme settling than the standard emulsions. In addition, the onset of phase separation in the small particle size nanoemulsions at 55° C. is later than for the standard emulsions.

Second, the small particle size nanoemulsions perform equal to or better than standard emulsions in inactivating bacteria. In a disinfectant test, the small particle size nanoemulsions exhibit a less than 1% failure rate against *Staphylococcus aureus* compared to greater than 5% for a standard nanoemulsion. In the same test, both the and standard nanoemulsion have a 0% failure rate against *Salmonella choleraesuis*. In a tube rotation test, the small particle size nanoemulsions have a slightly improved killing compared with the standard emulsions against *Staphylococcus aureus* killing activity.

While the invention is described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention. All references and publications cited herein are incorporated by reference in their entireties.

What is claimed is:

1. A composition comprising a nanoemulsion, the nanoemulsion consisting essentially of:

(a) about 5% by volume polyoxyethylene (20) sorbitan monolaurate;
(b) about 8% by volume ethanol;
(c) about 1% by volume cetylpyridinium chloride;
(d) about 64% by volume soybean oil;
and the balance is water,
wherein the nanoemulsion particles have an average diameter of less than about 200 nm, and the nanoemulsion has a milky white appearance.

2. The composition of claim 1 further comprising about 2 mM ethylenediaminetetraacetic acid.

3. The composition of claim 1, further comprising acyclovir.

4. The composition of claim 1, wherein the composition is capable of inactivating herpes labialis.

5. The composition of claim 1, wherein the composition is capable of inactivating a fungus or a dermatophyte causing an onychomycosis infection.

\* \* \* \* \*